United States Patent
Liphardt et al.

(10) Patent No.: US 7,317,529 B1
(45) Date of Patent: Jan. 8, 2008

(54) ASPECTS OF PRODUCING, DIRECTING, CONDITIONING, IMPINGING AND DETECTING SPECTROSCOPIC ELECTROMAGNETIC RADIATION FROM SMALL SPOTS ON SAMPLES

(75) Inventors: Martin M. Liphardt, Lincoln, NE (US); Ping He, Lincoln, NE (US); Blaine D. Johs, Lincoln, NE (US); Galen L. Pfeiffer, Lincoln, NE (US); James D. Welch, Omaha, NE (US); John A. Woollam, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 464 days.

(21) Appl. No.: 10/928,429

(22) Filed: Aug. 27, 2004

Related U.S. Application Data

(63) Continuation of application No. 10/699,540, filed on Nov. 1, 2003, now Pat. No. 7,158,231, and a continuation-in-part of application No. 10/613,051, filed on Jul. 7, 2003, now Pat. No. 7,099,006, and a continuation-in-part of application No. 10/425,801, filed on Apr. 29, 2003, now Pat. No. 6,930,813, and a continuation-in-part of application No. 09/583,229, filed on May 30, 2000, now Pat. No. 6,804,004, and a continuation-in-part of application No. 09/419,794, filed on Oct. 18, 1999, now Pat. No. 6,549,282.

(60) Provisional application No. 60/576,466, filed on Jun. 3, 2004, provisional application No. 60/572,204, filed on May 18, 2004, provisional application No. 60/553,032, filed on Mar. 15, 2004, provisional application No. 60/527,638, filed on Dec. 8, 2003, provisional application No. 60/527,554, filed on Dec. 6, 2003, provisional application No. 60/517,566, filed on Nov. 6, 2003, provisional application No. 60/498,479, filed on Aug. 28, 2003, provisional application No. 60/473,616, filed on May 28, 2003.

(51) Int. Cl.
*G01N 21/88* (2006.01)

(52) U.S. Cl. .................... 356/369; 356/237.1

(58) Field of Classification Search ........ 356/364–369, 356/237.1–237.5; 250/225
See application file for complete search history.

(56) References Cited

U.S. PATENT DOCUMENTS

| | | | |
|---|---|---|---|
| 3,748,015 A | 7/1973 | Offner | 350/55 |
| 4,175,864 A | 11/1979 | Gilby | 356/326 |
| 5,192,865 A | 3/1993 | Zhu | 250/288 |
| 5,233,156 A | 8/1993 | Chan et al. | 219/121.52 |
| 5,259,254 A | 11/1993 | Zhu et al. | 73/864.81 |
| 5,382,804 A | 1/1995 | D'Silva | 250/493.1 |
| 5,608,526 A | 3/1997 | Piwonka-Corle et al. | 256/369 |

(Continued)

OTHER PUBLICATIONS

Japanese Abstract 2003-307491, published Oct. 31, 2003.

*Primary Examiner*—Hoa Q. Pham
(74) *Attorney, Agent, or Firm*—James D. Welch

(57) ABSTRACT

Systems and methods for providing and enhancing electromagnetic radiation beam radial energy homogeneity and intensity vs. wavelength content, for reliably directing electromagnetic radiation emitted by a source thereof in a common direction, for achromatically reducing spot size on a sample (eg. liquid cavity containing lenses and low aberration 1:1 imaging systems modified to perform as spatial filters), and for directing different wavelengths into different detectors, in ellipsometer, polarizer or the like systems.

28 Claims, 15 Drawing Sheets

U.S. PATENT DOCUMENTS

| | | | |
|---|---|---|---|
| 5,666,201 A | 9/1997 | Johs et al. | 356/369 |
| 5,859,424 A | 1/1999 | Norton et al. | 250/226 |
| 5,872,630 A | 2/1999 | Johs et al. | 356/369 |
| 6,268,917 B1 | 7/2001 | Johs | 356/369 |
| 6,587,282 B1 | 7/2003 | Wang et al. | 359/797 |
| 6,907,059 B1 * | 6/2005 | Miura et al. | 372/98 |
| 7,173,716 B2 * | 2/2007 | Oishi et al. | 356/620 |
| 2006/0268271 A1 * | 11/2006 | Liphardt et al. | 356/369 |
| 2006/0268272 A1 * | 11/2006 | Liphardt et al. | 356/369 |

* cited by examiner

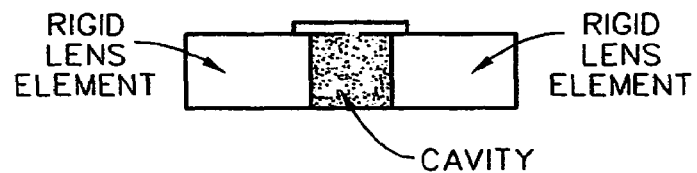
FIG. 8a
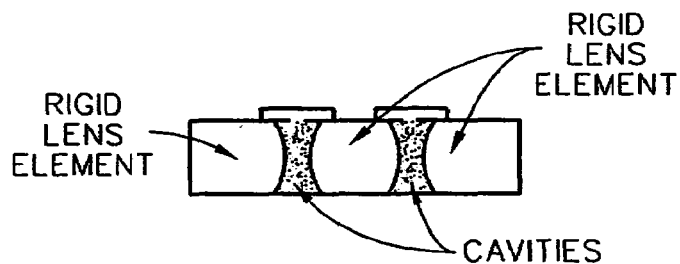
FIG. 8b
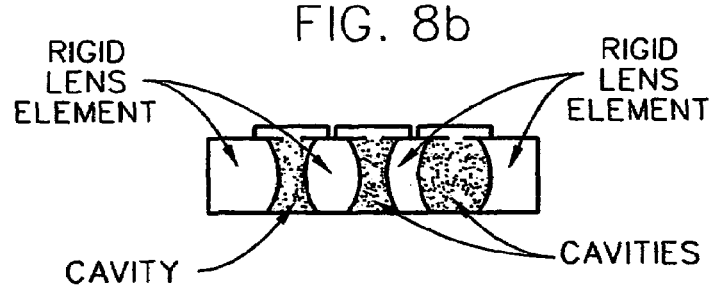
FIG. 8c
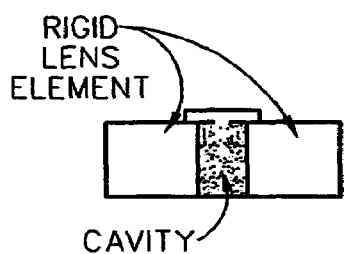 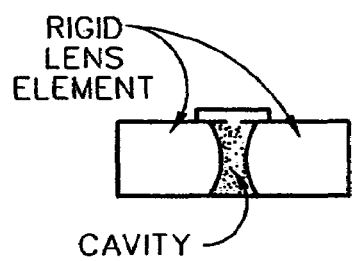 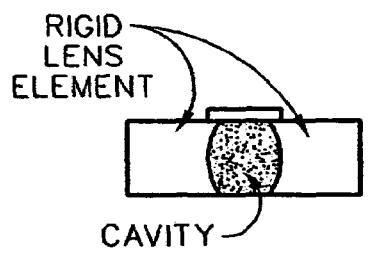
FIG. 8d  FIG. 8e  FIG. 8f
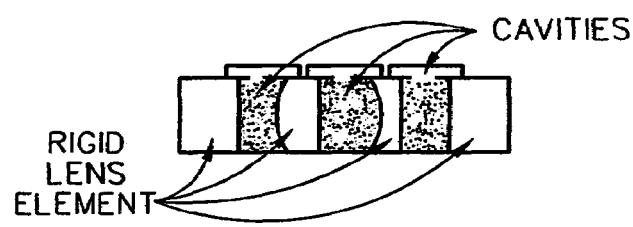
FIG. 8g

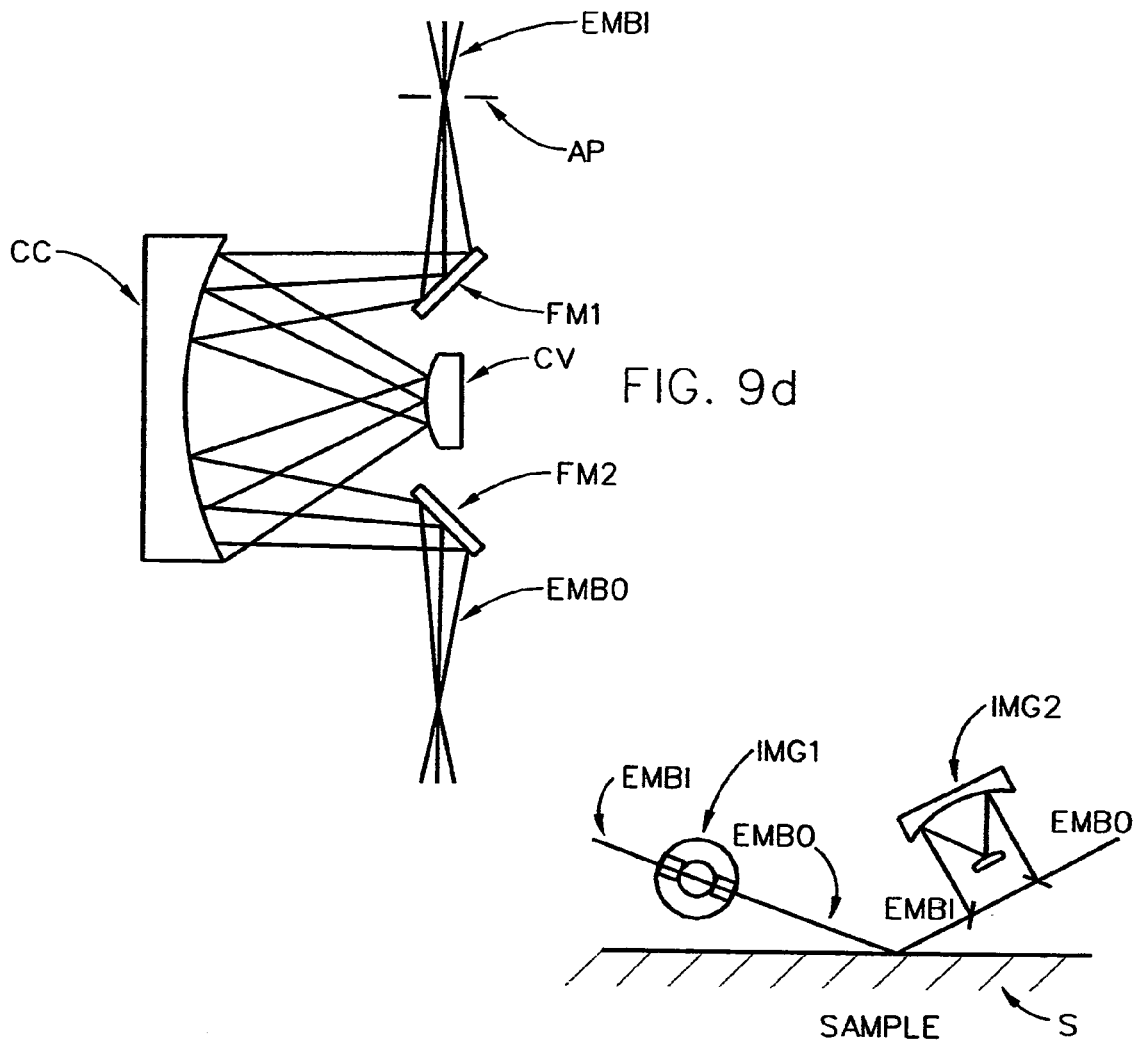
FIG. 9d
FIG. 9e
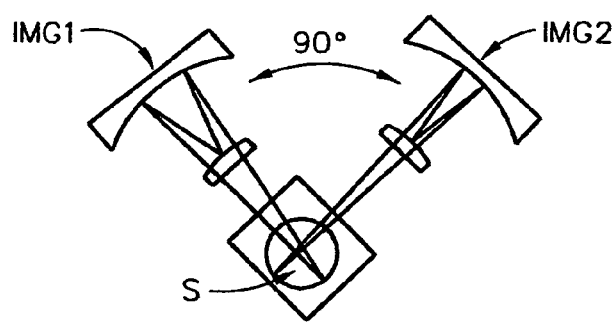
FIG. 9f

ASPECTS OF PRODUCING, DIRECTING, CONDITIONING, IMPINGING AND DETECTING SPECTROSCOPIC ELECTROMAGNETIC RADIATION FROM SMALL SPOTS ON SAMPLES

This application is a CIP of applications:
Ser. No. 09/583,229 May 30, 2000, (now U.S. Pat. No. 6,804,004);
 and therevia Ser. No. 09/419,794 Oct. 18, 1999 (now U.S. Pat. No. 6,549,282);
Ser. No. 10/613,051 Jul. 7, 2003, (now U.S. Pat. No. 7,099,006);
Ser. No. 10/699,540 Nov. 1, 2003, (now U.S. Pat. No. 7,158,231);
Ser. No. 10/425,801 Apr. 29, 2003, (now U.S. Pat. No. 6,930,813);

and Claims Benefit, therevia or directly, of Provisional applications:
 60/473,616 May 5, 2003; (via the 540 application)
 60/553,032 Mar. 15, 2004;
 60/517,566 Nov. 6, 2003;
 60/572,204 May 18, 2004;
 60/527,554 Dec. 6, 2003;
 60/527,638 Dec. 8, 2003;
 60/576,466 Jun. 3, 2004;
 60/498,479 Aug. 28, 2003.

TECHNICAL FIELD

The disclosed invention relates to ellipsometer and the like systems, and more particularly to means for producing, conditioning, directing and detecting electromagnetic radiation beams of desired wavelength content in ellipsometer and the like systems, comprising:
 source means for producing desired electromagnetic radiation wavelength content;
 means for reliably directing electromagnetic radiation emitted from a source thereof in a common direction;
 means for emphasizing relative intensity of electromagnetic radiation emitted by a source at wavelengths in desired ranges;
 means for achromatically reducing spot size of an impinging beam of electromagnetic radiation on a sample, including liquid containing lenses and low aberration 1:1 imaging systems configured to image, for instance, an aperture, and perform as spatial filters rather than focus a collimated beam onto said sample; and
 means for distributing electromagnetic radiation in defined wavelength bands into different detectors after interaction with a sample, based on wavelength.

BACKGROUND

Ellipsometry is a well known means by which to non-destructively monitor material systems, (samples). In brief, a polarized beam of electromagnetic radiation of one or more wavelengths is caused to impinge upon a material system, (sample), along one or more angles of incidence and interact with said material system, (sample). Beams of electromagnetic radiation can be considered as comprised of two orthogonal components, (ie. "P" and "S"), where "P" identifies a plane which contains both an incident beam of electromagnetic radiation, and a normal to an investigated surface of a material system, (sample), being investigated, and where "S" identifies a plane perpendicular to the "P" plane and parallel to said surface of said material system, (sample). A change in polarization state in a polarized beam of electromagnetic radiation caused by interaction with a material system, (sample), is representative of properties of said material system, (sample). (Note, while an incomplete characterization, Polarization State basically refers to a magnitude of a ratio of orthogonal component magnitudes in a polarized beam of electromagnetic radiation, and a phase angle therebetween). Generally two well known angles, (PSI and DELTA), which characterize a material system, (sample), at a given Angle-of-Incidence, are determined by analysis of data and represent change in polarization state. Additional sample identifying information is often also obtained by application of ellipsometry, including layer thicknesses, (including thicknesses for multilayers), optical thicknesses, sample temperature, refractive indicies and extinction coefficients, index grading, sample composition, surface roughness, alloy and/or void fraction, parameter dispersal and spectral dependencies on wavelength, vertical and lateral inhomogenieties etc.

Continuing, Ellipsometer Systems generally include a source of a beam of electromagnetic radiation, a Polarizer means, which serves to impose a linear state of polarization on a beam of electromagnetic radiation, a Stage for supporting a material system, (sample), and an Analyzer means which serves to select a polarization state in a beam of electromagnetic radiation after it has interacted with a material system, (sample), and pass it to a Detector System for analysis therein. As well, one or more Compensator(s) can be present and serve to affect a phase angle change between orthogonal components of a polarized beam of electromagnetic radiation. A number of types of ellipsometer systems exist, such as those which include rotating elements and those which include modulation elements. Those including rotating elements include Rotating Polarizer (RP), Rotating Analyzer (RA) and Rotating Compensator (RC). The presently disclosed invention can comprise a Rotating Compensator Ellipsometer System. It is noted that Rotating Compensator Ellipsometer Systems do not demonstrate "Dead-Spots" where obtaining data is difficult. They can read PSI and DELTA of a Material System over a full Range of Degrees with the only limitation being that if PSI becomes essentially zero (0.0), one can't then determine DELTA as there is not sufficient PSI Polar Vector Length to form the angle between the PSI Vector and an "X" axis. In comparison, Rotating Analyzer and Rotating Polarizer Ellipsometers have "Dead Spots" at DELTA's near 0.0 or 180 Degrees and Modulation Element Ellipsometers also have "Dead Spots" at PSI near 45 Degrees. The utility of Rotating Compensator Ellipsometer Systems should then be apparent. Another benefit provided by fixed Polarizer (P) and Analyzer (A) positions is that polarization state sensitivity to input and output optics during data acquisition is essentially non-existent. This enables relatively easy use of optic fibers, mirrors, lenses etc. for input/output.

Known relevant patents include a patent to Johs et al., U.S. Pat. No. 5,872,630, from which the present application is derived as a CIP via intervening CIP applications. Said 630 patent describes:
 A spectroscopic rotating compensator material system investigation system comprising a source of a polychromatic beam of electromagnetic radiation, a polarizer, a stage for supporting a material system, an analyzer, a dispersive optics and at least one detector system which contains a multiplicity of detector elements, said spectroscopic rotating compensator material system investigation system further comprising at least one compensator(s) positioned at a location selected from the group consisting of:
  before said stage for supporting a material system;
  after said stage for supporting a material system; and
  both before and after said stage for supporting a material system;
such that when said spectroscopic rotating compensator material system investigation system is used to investigate a material system present on said stage for supporting a material system, said analyzer and polarizer are maintained essentially fixed in position and at least one of said at least one compensator(s) is caused to continuously rotate while a polychromatic beam of electromagnetic radiation produced by said source of a polychromatic beam of electromagnetic radiation is caused to pass through said polarizer and said compensator(s), said polychromatic beam of electromagnetic radiation being also caused to interact with said material system, pass through said analyzer and interact with said dispersive optics such that a multiplicity of essentially single wavelengths are caused to simultaneously enter a corresponding multiplicity of detector elements in said at least one detector system.

Said 630 patent also, amongst other disclosure, describes a Mathematical Regression based Calibration procedure which makes possible the use of essentially any compensator regardless of non-achromatic characteristics.

Another patent to Johs, from which the 630 patent was Continued-in-Part, is No. 5,666,201, filed Sep. 20, 1995. The focus in said 201 patent comprises a detector arrangement in which multiple orders of a dispersed beam of electromagnetic radiation are intercepted by multiple detector systems. However, Claim 8 in the 201 patent, in combination with a viewing the Drawings therein, provide conception of the Spectroscopic Rotating Compensator Ellipsometer, as Claimed in Claim 1 of the JAW 630 patent and, in fact, the 630 patent issued in view of a Terminal Disclaimer based upon the 201 patent. A CIP of the 630 patent, is U.S. Pat. No. 6,353,477 to Johs et al. which describes preferred multiple element compensators.

It is known to generate polychromatic electromagnetic radiation by establishing a plasma, such as an inductively coupled plasma. It is also known to apply such plasma generated polychromatic electromagnetic radiation in polychromatic investigation of samples. For instance, it is known to inject particulate samples into plasmas and monitor an emitted wavelength spectrum to identify the chemical composition thereof. Recently, 31 Oct. 2003 a Japanese Abstract 2003-307491 was published, based upon Japanese Application 2003-048215, filed 21 Jan. 2003. Said Abstract discloses a system for and use of plasma generated polychromatic electromagnetic radiation to provide a beam which is directed through apertures and lenses to impinge upon a sample. After the resulting interaction with said sample, said polychromatic electromagnetic radiation is applied to characterize said sample. Application is in a Spectrometer system.

A patent to Zhu et al., U.S. Pat. No. 5,259,254 is disclosed to show that it is known to apply Inductively Coupled Plasma (ICP) in exciting Analytes. Patent to Chen et al., U.S. Pat. No. 5,233,156, is disclosed to show that (ICP) Torches are known. And, U.S. Pat. No. 5,192,865 to Zhu is disclosed to show that it is known to excite atoms into a Metastable state using an (ICP) system, followed by injecting Analyte into a multiplicity of said excited atoms, and direct the result through a skimmer and into a Mass Spectrometer. The invention in the Japanese Application 2003-048215 performs a similar function, with the beam of excited atoms being directed through a Skimmer in a Mass Spectrometer-like apparatus, and further provides a lens after said Skimmer which focuses electromagnetic radiation emitted from said Metastable Atoms. The Japanese 215 Application also shows that the beam of excited atoms is directed through said skimmer at an angle so as not to impact the lens, which lens is positioned such that were the Metastable atoms not entered at said angle, they would impinge thereupon.

Another patent, U.S. Pat. No. 5,382,804 to D'Silva describes photoionization lamp sources constructed from machinable photon radiation transparent material, such as crystalline magnesium or lithium fluoride which pass wavelengths emitted by excited Argon, Krypton and Xenon at 11.8, 10.2 and 9.5 eV respectively. This can be further described as low pressure discharge Argon provides an emitted wavelength of 104.8 NM, Xenon at 146.5 NM and Kyrpton at 123.5 NM. And of course, combinations of gasses can be utilized.

Another patent which describes a system for providing an output beam of polychromatic electromagnetic radiation which has a relatively broad and flattened intensity vs. wavelength characteristic over a wavelength spectrum is U.S. Pat. No. 6,268,917. Said patent describes a system comprising at least a first and a second source of polychromatic electromagnetic radiation and at least a first electromagnetic beam combining means. Said at least a first electromagnetic beam combining means is positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means. Said resultant beam of polychromatic electromagnetic radiation substantially is said output beam of polychromatic electromagnetic radiation which has a relatively broad and flattened intensity vs. wavelength over a wavelength spectrum, comprising said comingled composite of a plurality of input beams of polychromatic electromagnetic radiation which individually do not provide such a relatively broad and flattened intensity vs. wavelength over a wavelength spectrum characteristic.

It is further known to develop high temperature plasmas, which emit an essentially Black Body Spectrum, in magnetically contained small volumes which appear as point sources some distance therefrom, when viewed axially.

Benefit results from the application of custom wavelength content electromagnetic radiation in ellipsometer or the like systems. In particular, a plasma can be customized as regards its wavelength emission via the inclusion of selected analytes in a gas, (eg. argon), in which it is formed, and by selection of the carrier gas.

It is also generally known that many sources of electromagnetic radiation which provide wavelengths down to and below 193 nm typically provide said wavelengths at a lower intensity than is associated with longer, (eg. visible range), wavelengths. Further, it is known that optical elements through which electromagnetic radiation is caused to pass often have different effects on different wavelengths, (ie.

dispersal occurs), with a result being that electromagnetic radiation of one wavelength proceeds along a different path than does electromagnetic radiation of a different wavelength. Where said electromagnetic radiation is to be focused onto a spot on a sample said dispersion leads to the spot being of a diameter greater than 35 micron. In that light, it is disclosed that it is also known to place a lens in the path of a beam of electromagnetic radiation to, for instance, focus or collimate it. It is further known that single element lenses have different refractive effects on different wavelengths. Multiple element lenses, wherein at least two elements are present and are made of different materials, are known to more achromatic and uniformly refract different wavelengths. A consideration in constructing previously known multiple element lenses involves physical interconnection between elements. Rigid elements must be shaped to sequentially fit one element to the next. It would be of benefit if a generic system could be provided which could be tailored to have desired achromatic effects on multiple wavelengths without modifying rigid components.

It is also known in the art to focus a broadband beam of electromagnetic radiation onto a small spot in ellipsometers by reflective, as well as refractive optics. Typically, said prior art systems image a small aperture onto a spot on a sample with high demagnification, and, particularly where refractive optics are used, suffer from varying degrees of optical aberrations, (eg. spherical, chromatic, astigmatism etc.). In addition, surfaces of mirrors can be non-ideal as a result of non-traditional manufacturing of special optics, and the cost of non-spherical optics is high. It is also known that spherical optics can be fashioned to image an object with 1:1 magnification with essentially no aberrations. Such a 1:1 imager is, for instance, disclosed in an expired U.S. Pat. No. 3,748,015 which describes an imaging system comprising two elements:

a) a concave spherical mirror; and
c) a convex spherical mirror;

said elements being arrange such that electromagnetic radiation caused to approach the concave spherical reflects at a first location thereon is reflected to said a convex spherical mirror, from which it reflects onto a second location of said concave spherical mirror, from which it reflects as a beam of electromagnetic radiation, which, if the electromagnetic radiation caused to approach the concave spherical mirror at a first location was, for instance, an imaged aperture, appears as a small spot on the sample. It is emphasized that a collimated electromagnetic beam is not "focused" by the 1:1 imager, but rather a substantially point source is imaged thereby.

Other patents, U.S. Pat. No. 5,859,424 to Norton and U.S. Pat. No. 5,608,526 to Piwonka-Corle et al., are of interest as they describe focusing a collimated beam using a curved reflective mirror. This, it is noted, is in contrast to imaging a point source onto, for instance, a sample, as the 1:1 imaging system described in Expired U.S. Pat. No. 3,748,015 can be applied to accomplish in an ellipsometer system, (emphasis added).

A patent to Gilby, U.S. Pat. No. 4,175,864 is disclosed as it describes use of spherical and flat mirrors to focus a light slit.

The disclosed invention provides sources of electromagnetic radiation which provide desired wavelength output; means for improving relative intensity of electromagnetic radiation emitted by a source at wavelengths in, for instance, IR ad UV ranges; means for directing electromagnetic radiation emitted by a source along a desired locus; and reflective imaging and refractive focusing means for achromatically providing a small spot size of electromagnetic radiation where it is caused to impinge upon a sample surface.

DISCLOSURE OF THE INVENTION

As indicated in the Background Section, Ellipsometry provides a technique for determining the Dielectric Constant as well as physical properties of samples. Basically, electromagnetic radiation, which can be monochromatic or spectroscopic, of a known polarization state is caused to interact with a sample, reflect from or transmit therethrough and enter a detector wherein the polarization state is monitored. Changes in polarization state are at least partially attributable to interaction with the sample and are expressed as sample PSI ($\lambda$) and DELTA ($\Delta$) for a particular angle-of-incidence (AOI) and Wavelength, as defined by:

where rp and rs are orthogonal components of a beam of electromagnetic radiation in a plane perpendicular to the sample surface, and parallel thereto, respectively. For the purposes of the invention in this disclosure, the ellipsometer can be of any functional type, such as:

nulling;
rotating analyzer;
rotating polarizer;
rotating compensator;
modulation element;
and functional equivalents.

The disclosed invention provides, in the context of ellipsometer and the like systems, means for producing, directing, conditioning, and impinging spectroscopic electromagnetic radiation onto a small spot of a sample, then distributing reflected or transmitted electromagnetic radiation into a plurality of detectors based on wavelength, and comprises selections from the group consisting of:

source means for producing desired electromagnetic radiation wavelength content;
means for reliably directing electromagnetic radiation emitted from a source thereof in a common beam direction;
means for emphasizing relative intensity of electromagnetic radiation emitted by a source at wavelengths in desired ranges;
means for achromatically reducing spot size of an impinging beam of electromagnetic radiation on a sample, including liquid containing lenses and low aberration 1:1 imaging systems configured to image, for instance, an aperture, and perform as spatial filters rather than focus a collimated beam onto said sample; and
means for distributing electromagnetic radiation in defined wavelength bands into different detectors after interaction with a sample, based on wavelength.

Electromagnetic Beam Source

A first aspect of the disclosed invention comprises means for generating a polychromatic beam of electromagnetic radiation with a desired wavelength content, for application in a material system investigation system which comprises said source of a polychromatic beam of electromagnetic radiation, a polarizer means for imposing a state of polarization, a material system supporting stage, an analyzer means for detecting specific states of polarization, and a detector means which can direct different wavelengths into different detectors. Said material system investigation system can optionally comprise at least one compensator and/or aperture placed ahead of, and/or after said material system supporting stage. Also present is a processor for performing calculations that evaluate detector means intensity output signal.

In use said source of a polychromatic beam of electromagnetic radiation is caused to provide a beam of electromagnetic radiation and direct it to interact with a sample which is placed on said material system supporting stage after passing through said polarizer means, and then proceed through said analyzer means and into said detector means, which in turn produces data corresponding to intensity vs. angle-of-incidence and/or wavelength.

While not limiting, the material system investigation system can comprise apertures, (eg. at least four apertures between the source of a polychromatic beam of electromagnetic radiation and the material system supporting stage, and at least three apertures between the material system supporting stage and the detector means), through which the beam passes.

A present invention system can include a system for providing an output beam of polychromatic electromagnetic radiation which has a relatively broad and flattened intensity vs. wavelength characteristic over a wavelength spectrum, said output beam of polychromatic electromagnetic radiation substantially being a comingled composite of a plurality of input beams of polychromatic electromagnetic radiation which individually do not provide as relatively broad and flattened an intensity vs. wavelength characteristic over said wavelength spectrum as does said output comingled composite beam of polychromatic electromagnetic radiation. Said system comprises:

a. at least a first and a second source of polychromatic electromagnetic radiation; and b. at least a first electromagnetic beam combining means.

The at least a first electromagnetic beam combining means is positioned with respect to said first and second sources of polychromatic electromagnetic radiation such that a beam of polychromatic electromagnetic radiation from said first source of polychromatic electromagnetic radiation passes through said at least a first electromagnetic beam combining means, and such that a beam of polychromatic electromagnetic radiation from said second source of polychromatic electromagnetic radiation reflects from said at least a first electromagnetic beam combining means and is comingled with said beam of polychromatic electromagnetic radiation from said first source of polychromatic electromagnetic radiation which passes through said at least a first electromagnetic beam combining means. The resultant beam of polychromatic electromagnetic radiation is substantially the output beam of polychromatic electromagnetic radiation which has a relatively broad and flattened intensity vs. wavelength over a wavelength spectrum and comprises the comingled composite of a plurality of input beams of polychromatic electromagnetic radiation which individually do not provide such a relatively broad and flattened intensity vs. wavelength over a wavelength spectrum characteristic. The present invention system for providing an output beam of polychromatic electromagnetic radiation which has a relatively broad and flattened intensity vs. wavelength characteristic over a wavelength spectrum optionally further comprises:

a. a third source of polychromatic electromagnetic radiation; and b. a second electromagnetic beam combining means.

When present, the second electromagnetic beam combining means is positioned with respect to said comingled beam of polychromatic electromagnetic radiation which has a relatively broad and flattened intensity vs. wavelength over a wavelength spectrum and which exits said at least a first electromagnetic beam combining means, such that it passes through said second electromagnetic beam combining means. The second electromagnetic beam combining means is also positioned with respect to said third source of polychromatic electromagnetic radiation, but such that a beam of electromagnetic radiation from said third source of polychromatic electromagnetic radiation reflects from said second electromagnetic beam combining means such that a second resultant beam of polychromatic electromagnetic radiation is produced which is substantially an output beam of polychromatic electromagnetic radiation which has a relatively even more broadened and flattened intensity vs. wavelength over a wavelength spectrum, comprising a comingled composite of a plurality of input beams of polychromatic electromagnetic radiation from said first, second and third sources, which first, second and third sources individually do not provide such a relatively even more broadened and flattened intensity vs. wavelength over a wavelength spectrum characteristic.

Further, at least one of said first and second, (when present), electromagnetic beam combining means can be pivotally mounted in said system for providing an output beam of polychromatic electromagnetic radiation which has a relatively broad and flattened intensity vs. wavelength characteristic over a wavelength spectrum to allow rotation thereof, said rotation serving to comingle and direct transmitted and reflected beams of electromagnetic radiation along a common locus. Additionally, where the sources of electromagnetic radiation can be moved, the pivoting allows adjusting the angle at which a beam of polychromatic electromagnetic radiation from said second source of polychromatic electromagnetic radiation reflects from said at least one electromagnetic beam combining means. This allows control of the relative amounts of transmission and reflection effected by an electromagnetic beam combining means.

The disclosed material system investigation system can alternatively comprise a Plasma Source. One example thereof provides that the Plasma Source be an Inductively Coupled Plasma system comprising means for injecting a flow of carrier gas into a region of a Tube which is circumscribed by a Means for providing Electrical Excitation of an appropriate Frequency. Said Source of Polychromatic Electromagnetic Radiation can further comprise means for injecting an Analyte containing flow into the region of the Tube which is circumscribed by said Means for providing Electrical Excitation, such that in use the Analyte is injected into the region of the Tube which is circumscribed by said Means for providing Electrical Excitation and Electrical Energy is applied thereto, with the result being that a spectrum of wavelengths are emitted from the Tube. Said material system investigation system can further comprise at least one Lens positioned to collect some portion of said Spectrum of Wavelengths and direct said portion to said Polarizer.

The disclosed material system investigation system can comprise a Plasma based Source of Electromagnetic Radiation which comprises a Means for providing Electrical Excitation along a central axis in a Tube whereat is produced a plasma, and an extraction Enclosure which receives a Beam comprised of ions and excited atoms derived from the Plasma. Said Plasma based Source of Electromagnetic Radiation can further comprise an Optical Lens which collects luminous radiation emitted from the Plasma Beam, and a sighting device which comprises a metallic structure which is Substantially Cylindrical comprising an Input Aperture for the Plasma Beam. Said Plasma Beam comprised of ions and excited atoms can be directed at said lens so that said lens is exposed directly to said Plasma Beam, or preferably directed so that lens is not exposed directly to said Plasma Beam by said sighting device.

Another source of electromagnetic radiation can comprise a photoionization lamp of the type containing gas and electrodes for providing electrical excitation, in which the improvement comprises fabrication thereof in a block of machinable photon radiation transparent material such that said contained gas and electrodes are within a hole machined thereinto, preferably without need for additional gas containing elements other than gas entry means, such that during use, radiation produced therein by application of electrical energy to said electrodes can escape therefrom in essentially any direction not blocked by said electrodes.

Beam Directing

The disclosed invention provides that a beam of electromagnetic radiation can be produced by applying a back-reflector which is positioned to redirect electromagnetic radiation produced by a source thereof which is emitted in a direction other than in the direction of the beam, (ie. substantially 180 degrees opposite that of a desired beam). A disclosed system for improving characteristics of a spectroscopic beam of electromagnetic radiation directed in a "forward" direction from a source of electromagnetic radiation directing can comprise:

an off-axis parabolic mirror; and
a flat reflecting means;

said off-axis parabolic mirror being positioned to receive electromagnetic radiation from said source, and being positioned substantially in a "backward" projection direction 180 degrees rotated from said "forward" direction, and said flat reflecting means being positioned to receive electromagnetic radiation which reflects from said off-axis parabolic mirror and via reflection direct it directly back to said off-axis parabolic mirror, which off-axis parabolic mirror then directs it back through said source of electromagnetic radiation and along said "forward" direction;

the effect being increased intensity in said "forward" directed beam.

The flat reflecting means can uniformly reflect all wavelengths.

The flat reflecting means can reflect different wavelengths with different efficiencies.

The flat reflecting means can reflect IR and UV wavelengths more efficiently than visual range wavelengths.

The flat reflecting means can comprise semiconductor.

The flat reflecting means can comprise silicon.

The flat reflecting means can comprise silicon with a thin film of other material on its reflective surface, and a typical non-limiting material on said reflective surface is SiO2.

A variation of the system for improving characteristics of a spectroscopic beam of electromagnetic radiation directed in a "forward" direction from a source of electromagnetic radiation directing comprises:

a concave mirror;

said concave mirror being positioned to receive electromagnetic radiation from said source, and being positioned substantially in a "backward" projection direction 180 degrees rotated from said "forward" direction;

such that electromagnetic radiation from said source thereof which is directed in the "backward" direction is reflected from said concave mirror in a "forward" direction;

the effect being increased intensity in said "forward" directed beam.

The concave mirror can comprise semiconductor, such as silicon, or silicon with a thin film of other material on its reflective surface, (eg. a typical non-limiting material is SiO2).

Another variation of a system for improving characteristics of a spectroscopic beam of electromagnetic radiation directed in a "forward" direction from a source of electromagnetic radiation directing comprises:

a flat reflecting means; and
a spherical mirror;

said flat reflecting means being positioned to receive electromagnetic radiation from said source, and being positioned substantially in a "backward" projection direction 180 degrees rotated from said "forward" direction, and said spherical mirror being positioned to receive electromagnetic radiation which reflects from said flat reflecting means and via reflection direct it directly back to said flat reflecting means, which flat reflecting means then directs it back through said source of electromagnetic radiation and along said "forward" direction;

the effect being increased intensity in said "forward" directed beam.

The flat reflecting means can uniformly reflect all wavelengths, or can reflect different wavelengths with different efficiencies, (eg. reflect IR and UV wavelengths more efficiently than visual range wavelengths), or can comprise semiconductor, (eg. silicon, or silicon with a thin film of other material on its reflective surface such as SiO2).

While Back-reflectors are beneficial, it has been found that over time they can become less efficient as a result of deposits onto the reflective surface thereof. Another aspect of the present invention provides that a back-reflector be placed into a container which has openings present to allow the flow of gas into, through and out thereof, as well as allow electromagnetic radiation to enter thereinto and exit therefrom. It has been found that the gas flow prevents accumulation of deposits onto the back-reflector surface.

A present invention system for providing a beam of electromagnetic radiation can be described as comprising:

a source of electromagnetic radiation; and
a back-reflector having a reflective surface;

said back-reflector being situated with respect to said source of electromagnetic radiation such that at least some electromagnetic radiation emitted in a direction other than that of the beam of electromagnetic radiation, is redirected into the direction of said beam of electromagnetic radiation thereby;

said system being characterized in that said back-reflector is in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface.

As applied in an ellipsometer system, the present invention can be described as comprising a source of electromagnetic radiation, a polarizer, a stage for supporting a sample, an analyzer and a detector, there optionally being at least one compensator present between said polarizer and stage and/or between said stage and analyzer;

such than in use a beam of electromagnetism is caused to be directed by said source thereof toward a sample placed on said stage, interact with said sample, pass through said analyzer and enter said detector, said beam also passing through any present compensator, said source of electromagnetic radiation comprising a back-reflector having a reflective surface, said back-reflector being situated in said source of electromagnetic radiation such that at least some electromagnetic radiation emitted in a direction other than that of the beam of electromagnetic radiation, is redirected into the direction of said beam of electromagnetic radiation thereby; said back-reflector being in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface.

A method of characterizing a sample comprises the steps of:

a) providing an ellipsometer system as just described;

b) placing a sample onto said stage;

c) simultaneously causing:
said source of electromagnetic radiation to provide a beam of electromagnetic radiation and direct it to pass through said polarizer, interact with said sample and enter said detector, and through any compensator present;
causing gas to flow into and out of said container;

and analyzing signals produced by said detector to characterize said sample.

Said system for investigating a sample can further comprise:
a) a polarizer between said source and sample; and
b) an analyzer between said sample and detector;

and constitute an ellipsometer, and if a compensator is present between said source and detector, a polarimeter results.

Beam Conditioning

Another aspect of the disclosed invention addresses conditioning, as well as directing electromagnetic radiation produced by a source thereof along a desired locus. As already identified, a problem with many Sources of Electromagnetic Radiation is that they emit radiation along other than a desired beam path. Further, many Sources provide radiation of a relatively high intensity between the Ultra-violet and Infrared, but drop off quickly in the UV and IR. That is, generally, Sources of Electromagnetic Radiation often provide wavelength/intensity characteristics which are less than perfect for certain Ellipsometric applications.

One already identified approach is to improving the characteristics of a Source of Electromagnetic Radiation is to provide a back reflector, behind a source of electromagnetic radiation, which serves to direct electromagnetic radiation which exits the source in a useful forward direction. This increases Intensity generally. Based on the nature of the Back Reflector, however, it is possible to selectively enhance Intensity in some wavelengths as opposed to others.

For instance, it is possible to provide a reflecting means in the pathway of an electromagnetic beam, upon which reflecting means is a coating which emphasizes reflection of the UV, (eg. at 193 nm), relative to non-UV range wavelengths. An example of such a coating on a reflective means is 600 to 1200 Angstroms, for instance, of Silicon Dioxide on Silicon. This approach enables setting "gain" providing means at higher levels to emphasize UV signals, while not over amplifying, and even saturating higher intensity, (eg. Visible), wavelengths signals. Back Reflectors can be comprised of such reflective materials, or a separate reflecting elements can be placed in a Beam of Electromagnetic Radiation between a Source and Detector.

A disclosed invention material system investigation system can then comprise a source of a polychromatic beam of electromagnetic radiation, a polarizer, a material system supporting stage, an analyzer and a detector, and a processor for performing calculations that evaluate detector output signal, there optionally being present at least one compensator between said polarizer and analyzer; said material system investigation system being characterized in that there is present in the pathway of polychromatic beam at least one reflective element which reflects more efficiently in wavelength ranges in which the intensity from the source is less intense as compared to wavelengths in ranges in which the intensity from the source is of relatively higher intensity. In use said source of a polychromatic beam of electromagnetic radiation is caused to provide a beam of electromagnetic radiation which is directed to interact with a sample which is placed on said material system supporting stage after passing through said polarizer, then after interaction with said sample, through said analyzer and into said detector, which in turn produces data corresponding to a parameter vs. angle-of-incidence or wavelength or mathematical equivalent, said polychromatic beam of electromagnetic radiation also being caused to reflect from said at least one reflective element at a point between said source of a polychromatic beam of electromagnetic radiation and said detector.

Production of Small Spot Size on Sample

The just described material system investigation system can further comprise at least one achromatic lens before and/or after said sample, said at least one achromatic lens being characterized by a selection from the group consisting of:

a) it comprises at least one cavity which contains flowable material selected from the group consisting of:
powder;
fluid; and
liquid;
water base liquid;
oil base liquid;

b) it comprises at least one cavity having at least one concave side at an interface between an effective element and a cavity boundary;

c) it comprises at least one cavity having at least one convex side at an interface between an effective element and a cavity boundary;

d) it comprises at least one cavity having at least one side at an interface between an effective element and a cavity boundary;

e) it comprises at least one cavity having two concave sides at an interfaces between an effective element and a cavity boundaries;

f) it comprises at least one cavity having two convex sides at an interfaces between an effective element and a cavity boundaries;

g) it comprises at least one cavity having two flat sides at an interfaces between an effective element and a cavity boundaries;

h) it comprises at least one cavity having one concave side and one convex interface between an effective element and a cavity boundaries; and i) it comprise at least one cavity having one concave side and one flat interface between an effective element and a cavity boundaries.

The disclosed invention can then comprise a lens system with at least one cavity therein, said cavity having means for entering a flowable material such as a powder, fluid or liquid thereinto. Depending on the fluid entered to said at least one cavity, a system comprising an effective multi-element lens with refractive properties at various wavelengths which depend on the flowable material caused to be present in said cavity is effected. Further, the flowable material can be removed from the cavity and replaced by another, thereby providing a system with different refractive properties at various wavelengths. It should be appreciated that a filled cavity is an effective lens element in the disclosed invention system. It is to also be appreciated that a multiple cavity system can have different flowable materials present in at least two of the cavities, thereby allowing the achieving of desired refraction at various wavelengths. Quasi achromatic lenses can be achieved in this way.

Another approach to improving optical element characteristics is to coat transmissive elements, such as lenses present in the system, to minimize entry and exit losses caused thereby, and improve overall UV transmission therethrough. An example is a single 300 Angstrom layer of $MgF_2$. Multilayer coatings can also be used.

Another approach to conditioning electromagnetic beams is to provide a Grating which has characteristics that emphasize UV wavelengths and/or direct a utilized "Order" of wavelengths in a direction which is subject to less influence by the zero and/or other orders.

Further, application of baffling to block access of zero and/or other orders of electromagnetic radiation to detector means can be applied.

If attenuation of UV wavelengths thereby is not considered prohibitive, optical fibers can be applied. However, if optical fibers are utilized, to reduce loss of UV intensity at fiber entry, a narrow (eg. smaller that the fiber dimension), beam can be focused at the entry to the fiber.

It is also disclosed that the following approaches, which focus on increasing the amount of UV electromagnetic radiation, can be practiced independently or in combination:

Utilize a source of electromagnetic radiation which emphasizes UV wavelength production. Various wattage lamps (eg. 35, 75 and 150 can be applied and where necessary can involve application of various indirect heat sink based cooling and produced ozone containment.

In the case of rotating compensator ellipsometers, reduce the rotation speed of the compensator so that for the same number of rotations more total electromagnetic radiation passes therethrough and reaches the detector.

Take multiple scans of data to improve signal to noise.

Combine the output of multiple pixels in a detector which receive UV radiation.

An approach which is focused on providing a small spot size, (eg. 35 mm), is to identify optical elements which enter dispersion of wavelengths entered thereinto and reduce their effect. Dispersion, it should be appreciated causes different wavelengths in electromagnetic radiation to focus at different points on a sample. Reduced dispersion can be accomplished by, for instance, adding optical elements which offset the effect entered by existing optical elements. While increasing physical dimensions and potentially adding entry and exit and transmission attenuation effects, the result can be a smaller spot size.

Another approach to providing a small are spot on a sample is to apply a 1:1 Imager, which images a point source or aperture onto a sample as opposed to focusing a collimated beam. One embodiment of a disclosed invention Imager system is a combined spatial filter and imaging system comprising three elements:

a) a concave spherical mirror having at least one concave spherical surface and an aperture hole therethrough;

b) a flat mirror; and c) a convex spherical mirror having at least one convex spherical surface.

Said elements are arranged such that electromagnetic radiation caused to approach the concave spherical mirror passes through said aperture hole and reflects from said flat mirror onto a first location of a concave surface of said concave spherical mirror. It then reflects from said first location onto a convex spherical surface of said convex spherical mirror and reflects therefrom onto a second location of said concave surface of said concave spherical mirror as a converging beam of electromagnetic radiation.

Another embodiment of a disclosed combined spatial filter and imaging system comprises:

a) an aperture;

b) a flat mirror;

c) a concave spherical mirror having at least one concave spherical surface; and d) a convex spherical mirror having at least one convex spherical surface.

Said elements are arranged such that electromagnetic radiation which images said aperture is caused to approach the flat mirror and reflect therefrom onto a first location of a concave surface of said concave spherical mirror. It then reflects from said first location onto a convex spherical surface of said convex spherical mirror and reflects therefrom onto a second location of said concave surface of said concave spherical mirror from which it reflects as a converging beam of electromagnetic radiation.

Said embodiment can include a second flat mirror positioned to intercept and reflect electromagnetic radiation reflected from said second location of said concave surface of said concave spherical mirror as a converging beam of electromagnetic radiation. Said modified second embodiment then comprises five elements:

a) an aperture;

b) a first flat mirror;

c) a concave spherical mirror having at least one concave spherical surface;

d) a convex spherical mirror having at least one convex spherical surface; and e) a second flat mirror.

Said elements are arranged such that electromagnetic radiation which images said aperture is caused to approach the first flat mirror and reflect therefrom onto a first location of a concave surface of said concave spherical mirror. It reflects from said first location onto a convex spherical surface of said convex spherical mirror and reflect therefrom onto a second location of said concave surface of said concave spherical mirror reflects therefrom onto said second flat mirror which is positioned to intercept and reflect electromagnetic radiation reflected from said second location of said concave surface of said concave spherical mirror as a converging beam of electromagnetic radiation.

In ellipsometry applications it is best to keep the angle of incidence of electromagnetic radiation onto a flat mirror low, (eg. less than 20 degrees). Where it is desired to use a larger angle, say 45 degrees, the presently disclosed invention can be advantageously modified. An example is a system for investigating a sample can then comprise:

a source of electromagnetic radiation;
an aperture;
first and second imaging systems, each thereof comprising four elements:
  a) a first flat mirror;
  b) a concave spherical mirror having at least one concave spherical surface;
  c) a convex spherical mirror having at least one convex spherical surface; and
  d) a second flat mirror.

Said elements are arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror onto said second flat mirror positioned to intercept and reflect electromagnetic radiation reflected from said second location of said concave surface of said concave spherical mirror as a converging beam of electromagnetic radiation;

and a detector;
said sample being positioned between said first and second imaging systems.

Said first imaging system is positioned to image electromagnetic radiation from the source thereof as it passes through said aperture and direct it onto a surface of said sample at an oblique angle of incidence, and said second imaging system is positioned to receive electromagnetic radiation reflected from the sample and pass it on to said detector, the propagation direction of electromagnetic radiation entering and exiting each of said first and second imaging systems being substantially unchanged by passing therethrough.

Said system is further characterized in that a plane formed by the locus of the electromagnetic radiation passing through the first imaging system is oriented 90 degrees to a plane formed by the locus of the electromagnetic radiation passing through the second imaging system, the purpose being to minimize effects of said first and second imaging systems on a polarization state of said electromagnetic radiation which passes through both thereof.

A modified system for investigating a sample comprises:
a source of electromagnetic radiation;
an aperture;
first and second imaging systems, each thereof comprising four elements:
  a) a first flat mirror;
  b) a concave spherical mirror having at least one concave spherical surface;
  c) a convex spherical mirror having at least one convex spherical surface; and
  d) a second flat mirror;

said elements being arranged such that electromagnetic radiation is caused to approach the first flat mirror and reflect therefrom onto a first location of a concave surface of said concave spherical mirror, reflect from said first location onto a convex spherical surface of said convex spherical mirror and reflect therefrom onto a second location of said concave surface of said concave spherical mirror onto said second flat mirror positioned to intercept and reflect electromagnetic radiation reflected from said second location of said concave surface of said concave spherical mirror as a converging beam of electromagnetic radiation;
and a detector;
said first and second imaging systems being positioned on the same side of the sample and having focusing means therebetween such that said second imaging system images a substantially point source;

the propagation direction of electromagnetic radiation entering and exiting each of said first and second imaging systems being substantially unchanged by passing therethrough;

said system being further characterized in that a plane formed by the locus of the electromagnetic radiation passing through the first imaging system is oriented 90 degrees to a plane formed by the locus of the electromagnetic radiation passing through the second imaging system, the purpose being to minimize effects of said first and second imaging systems on a polarization state of said electromagnetic radiation which passes through both thereof.

Distributing Electromagnetic Radiation into Detectors

After electromagnetic radiation in a spectrophotometer, reflectometer, ellipsometer or polarimeter or the like system interacts with a sample, it is directed into a Detector, and it is known that different types of Detectors are more sensitive to different wavelengths. With that in mind, it is disclosed that the disclosed invention further comprises a means for distributing electromagnetic radiation into different type Detectors based on Wavelength. A preferred approach is to provide a sequence of progressively decreasing Bandgap Material, each oriented to receive and direct reflected, shorter wavelength electromagnetic radiation into a specific detector while passing remaining longer wavelengths to the next smaller Bandgap Material. Of course partially reflecting partially transmitting mirrors, and beam splitters and the like can also be employed, but usually each simply divide the energy present in a full spectrum into two parts without providing beneficial Hi-Low Pass Filtering. Additionally, it is often beneficial to focus a Beam of Electromagnetic Radiation which is reflected from a sample onto the input of a Fiber Optic, which in turn guides the electromagnetic radiation into said Detector System. As disclosed elsewhere herein, where the Beam of Electromagnetic Radiation is focused onto the end of an Optical Fiber which is of a larger diameter than is the focused Beam, beneficial reduction in loss of intensity is achieved.

A material system investigation system can comprise a source of a polychromatic beam of electromagnetic radiation, a polarizer, a material system supporting stage, an analyzer and a detector, and a processor for performing calculations that evaluate detector output signal, there optionally being present at least one compensator between said polarizer and analyzer. Said material system investigation system being characterized in that the detector comprises a multiple detector system comprising a sequential plurality of decreasing bandgap materials, each being oriented to receive a beam of electromagnetic radiation and, while transmitting relatively long wavelengths therethrough, reflecting relatively shorter wavelengths therein, which wavelengths are sufficiently short as to have an energy in excess of the bandgap of said material into a detector appropriately positioned to intercept said reflected relatively shorter wavelengths, such that in use said source of a polychromatic beam of electromagnetic radiation is caused to provide a beam of electromagnetic radiation which is directed to interact with a sample which is placed on said material system supporting stage after passing through said polarizer, then after interaction with said sample, through said analyzer and direct each wavelength into a detector of said multiple detector system, which in turn produces data corresponding to a parameter vs. angle-of-incidence or wavelength or mathematical equivalent. Said material system investigation system can further comprise a converging lens and an optical fiber between said analyzer and multiple detector system, such that electromagnetic radiation passing through said analyzer are focused into said optical fiber and is directed thereby into said multiple detector system.

The disclosed invention can then comprise a system for conditioning intensity of wavelengths in spectroscopic electromagnetic radiation, said system comprising:

means for providing a beam of spectroscopic electromagnetic radiation;

an element which reflects an electromagnetic radiation in a beam of electromagnetic radiation caused to impinge thereupon at an oblique angle to the surface thereof, said reflected beam comprising shifted relative intensities between different wavelengths; and a detector positioned to intercept electromagnetic radiation reflected from said element.

In use a beam of spectroscopic electromagnetic radiation is caused to impinge on said element and at least partially reflect therefrom and enter said detector. An exemplary beam conditioning element comprises SiO2 on Si.

Note that a typical use for said system for conditioning intensity of wavelengths is in a system such as a spectroscopic ellipsometer or polarimeter or reflectometer or spectrophotometer and the like systems which provides that said beam of electromagnetic radiation interacts with a sample system, and that system(s) for conditioning intensity of wavelengths can be positioned before and/or after said sample.

The disclosed invention further comprises a system for providing wavelengths in defined ranges of wavelengths in spectroscopic electromagnetic radiation to different detectors comprising:

means for providing a beam of spectroscopic electromagnetic radiation;

at least one element which partially reflects and partially transmits electromagnetic radiation in a beam of electromagnetic radiation caused to impinge thereupon at an oblique angle to the surface thereof; and at least two detectors, one positioned to intercept electromagnetic radiation reflected from said element, and another to intercept electromagnetic radiation transmitted through said at least one element.

In use a beam of spectroscopic electromagnetic radiation is caused to impinge on said at least one element and partially reflect from and partially transmit therethrough, the transmitted and reflected electromagnetic radiation being directed into separate detectors.

In use a beam of spectroscopic electromagnetic radiation is caused to impinge on said at least one element and partially reflect from and partially transmit therethrough, the transmitted and reflected electromagnetic radiation being directed into separate detectors.

Exemplary embodiments of the at least one element are:

a material with a known bandgap selected from the group consisting of:

Si;
Ge;
GaN;
ZnSe;
ZnTe; and
ZnCd.

A more complex embodiment of the disclosed invention provides that the system for providing wavelengths in defined ranges of wavelengths in spectroscopic electromagnetic radiation, to different detectors, comprises:

means for providing a beam of spectroscopic electromagnetic radiation;

at least two elements, each of which has a substantially planar surface, and which have different characteristics with respect to one another regarding reflected and transmitted electromagnetic radiation in a beam of electromagnetic radiation caused to impinge thereupon at an oblique angle to the surface thereof;

at least two detectors, one positioned to intercept electromagnetic radiation reflected from one of said elements, and another to intercept reflected or transmitted electromagnetic radiation from another of said elements;

such that in use a beam of spectroscopic electromagnetic radiation is caused to impinge on a first of said at least two elements and partially reflect from and partially transmit therethrough, the transmitted portion then partially reflecting from and optionally partially transmitting through said second element, with reflected electromagnetic radiation from the first element and reflected or transmitted electromagnetic radiation from the second being directed into separate detectors.

Said system for providing wavelengths in different ranges of wavelengths in spectroscopic electromagnetic radiation to different detectors can utilize elements selected from the group consisting of:

a "polka-dot" beam splitter; and a material with a known bandgap selected from the group consisting of:

Si, Ge, GaN, ZnSe, ZnTe and ZnCd.

A "polka-dot" beam splitter such as Edmond Scientific part number 46-457 comprises a plate which is effectively half coated with a multiplicity of reflective regions. In use, substantially all wavelengths in a beam of electromagnetic radiation typically partially reflect from and partially transmit through said "polka-dot" beam splitter, and different detectors can be positioned to receive said similar wavelength content reflected and transmitted beams, typically via another reflective beam directing and optionally conditioning means. For instance, one detector might be sensitive to UV and the other to Visible or other wavelength range. Also, it is well known that semiconductors are transparent to wavelengths long enough to be of an energy less than their Band-Gap, but are opaque/reflective to wavelengths which are short enough to be absorbed thereby. Where a semiconductor such as Si, Ge, GaN, ZnSe, ZnTe and ZnCd is placed in the path of an electromagnetic beam such that said electromagnetic beam approaches at an oblique angle to the surface thereof, specific ranges of wavelengths will reflect therefrom and certain wavelengths will pass therethrough. Detectors sensitive to the relevant wavelength range can be positioned to intercept the reflected and transmitted beams.

In a sequence of a plurality of different Bandgap materials, the sequence of materials will typically have decreasing Bandgaps one to the next, and detectors associated with each material will be best suited for detecting sequentially longer wavelengths which are reflected therefrom. This is because larger Bandgap Materials are transparent to shorter wavelengths than are smaller Bandgap Materials, and reflection occurs at sequentially longer wavelengths as materials with sequentially smaller Bandgaps are encountered. Note, "sequentially positioned" means an element is positioned to receive transmitted electromagnetic radiation through a previous element of a larger Bandgap.

A method of detecting spectroscopic electromagnetic radiation then comprises the steps of:

a) providing a system for receiving electromagnetic radiation comprising at least one element which passes and which transmits wavelengths in known wavelength ranges;

b) causing a spectroscopic beam of electromagnetic radiation to approach each said element at an angle to the surface thereof such that reflected electromagnetic radiation is directed in first defined direction and such that transmitted electromagnetic radiation is directed in a second defined direction;

c) positioning a detector to intercept at least the reflected beam of electromagnetic radiation from the at least one element.

Said method can involve providing at least one element which passes and which transmits wavelengths in known different wavelength ranges, and providing at least two elements which have different characteristics in sequential functional combination with positioning detectors to intercept reflected beams of electromagnetic radiation from both thereof.

Said method can provide that each element is selected from the group consisting of:

a "polka-dot" beam splitter which reflects and transmits known percentages of an incident beam substantially equally at all wavelengths; and
a material with a known bandgap selected from the group consisting of:
Si, Ge, GaN, ZnSe, ZnTe and ZnCd;
which reflects and transmits wavelengths in different wavelength ranges.

Another aspect of the disclosed invention is to place elements with wavelength specific attenuating properties. For instance, spectroscopic electromagnetic radiation reflected from a Silicon Substrate with a coating of SiO2 (eg. 600-1500 Angstroms), present at its surface emphasizes intensity in the IR and UV. Such systems condition a beam of spectroscopic electromagnetic radiation emerging therefrom so that it has a different intensity profile with respect to wavelength than the incident beam.

Finally, it is noted that a disclosed invention reflectometer, spectrophotometer, polarimeter or ellipsometer can include, between said Source and Polarizer, a means for effecting a cross-sectional, essentially radially homogeneous energy density in an electromagnetic beam, said means comprising a sequential combination of:
beam expander;
first beam collimator;
at least one multi-faceted optical element;
beam condenser; and
second beam collimator;

such that in use electromagnetic radiation of arbitrary cross-sectional radial energy density is provided by said source of electromagnetic radiation and is caused to pass through said means for effecting cross-sectional, essentially radially-uniform energy density in electromagnetic beams such that a beam of substantially radially uniform energy density is output therefrom, is caused to interact with a sample system and then enter a detector.

The disclosed invention comprises an Ellipsometer, Polarimeter, Reflectometer or Spectrophotometer System which comprises elements as disclosed in the foregoing, and will be better understood by reference to the Detailed description Section.

SUMMARY OF THE INVENTION

It is therefore an objective and/or purpose of the disclosed invention to teach sources of electromagnetic radiation in reflectometer, spectrophotometer, ellipsometer, polarimeter or the systems, which sources enable structuring intensity vs. wavelength output content.

It is another objective and/or purpose of the disclosed invention to teach, in reflectometer, spectrophotometer, ellipsometer, polarimeter or the systems, back-reflector means for directing electromagnetic radiation emitted in a common direction.

It is yet another objective and/or purpose of the disclosed invention to teach, in reflectometer, spectrophotometer, ellipsometer, polarimeter or the systems, means for preventing function degrading deposits onto back-reflector means for directing electromagnetic radiation.

It is another objective and/or purpose yet of the disclosed invention to teach, in reflectometer, spectrophotometer, ellipsometer, polarimeter or the systems, means for electromagnetic beam intensity vs. wavelength conditioning.

It is still yet another objective and/or purpose of the disclosed invention to teach, in reflectometer, spectrophotometer, ellipsometer, polarimeter or the systems, means for presenting electromagnetic radiation onto small spot sizes on a sample.

It is another objective and/or purpose of the disclosed invention to teach, in reflectometer, spectrophotometer, ellipsometer, polarimeter or the like systems, means for distributing electromagnetic radiation in different wavelength ranges to different detectors.

BRIEF DESCRIPTION OF THE DRAWINGS

FIGS. 8a-8g show various Multiple Element Lenses which contain liquid filled-cavities.

FIGS. 9b-9f demonstrate 1:1 imaging systems based on the Offner 015 patent to image a point source onto a sample.

DETAILED DESCRIPTION

Figure 1A:
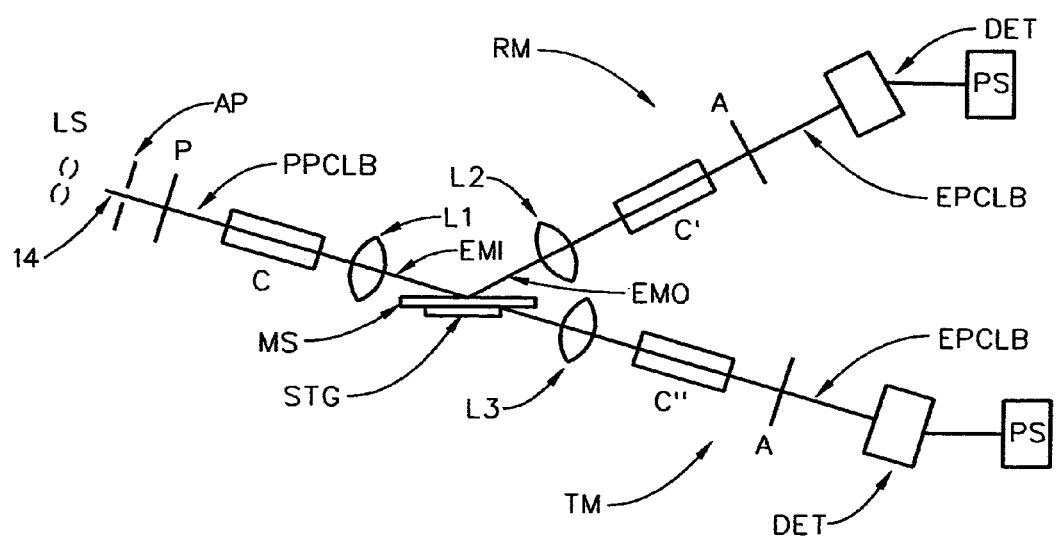
FIG. 1a shows the basic components of Reflectance and Transmission Mode Material System Investigation Systems.

FIG. 1a shows a demonstrative, non-limiting, ellipsometer system which can be applied to practicing the disclosed invention. There is demonstrated a Material System Investigation System, (ie. a Spectroscopic Ellipsometer System), with provision to investigate a Material System (MS) in either a Reflection Mode (RM) or a Transmission Mode (TM). It is to be noted that said Material System investigation System is generally comprised of a Source (LS) of a Polychromatic Beam (14) of Electromagnetic Radiation, (ie. a Broadband electromagnetic radiation source), a Polarizer Means (P), a Material System, supporting Stage (STG), an Analyzer Means (A) and a Detector Elements (DE's) containing Photo Array Detector Means System (DET). Also note, however, that FIG. 1a shows Reflection Mode System Compensator(s) Means (C) and (C') and Transmission Mode System Compensator(s) Means (C) and (C") as present. It is to be understood that a Compensator Means can be placed ahead of, and/or after a Material System (MS) supporting Stage (STG) in either a Reflection Mode or Transmission Mode System. That is only Compensator Means (C) or (C') or both Compensator Means (C) and (C') can be present in a Reflection Mode System (RM), and only Compensator Means (C) or (C") or both Compensator Means (C) and (C") can be simultaneously present in the Transmission Mode System (TM). FIG. 1a also shows the presence of a Processor (PS) for performing calculations that evaluate a sample based on the Detector (DET) intensity output signal. Also indicated are optional Apertures (AP), and Lenses (L1), (L2) and (L3).

It should be appreciated that the configuration in FIG. 1a could be operated as a Rotating Polarizer or Rotating Analyzer System. The disclosed Rotating Compensator Material System Investigation System, however, in the preferred operational mode, essentially fixes the Polarizer Means (P) and Analyzer Means (A) during Data Acquisition from a Material System (Sample) (MS) which is placed upon the Material System supporting Stage (STG), and causes at least one present Compensator Means ((C), and/or (C') or (C) and/or (C")), to Rotate during said Data Acquisition. This serves to effectively enter a continuously varying retardance between Orthogonal Components in a Polarization Beam of Electromagnetic Radiation exiting said Compensator Means which is caused to rotate. Where two (2) Compensator Means are present, one before (C) and one after ((C') or (C")) a Material System placed upon said Material System (MS) supporting Stage (STG), only one, or both said Compensator Means can be caused to Rotate in use. If both Compensator Means are caused to rotate, both can be rotated a the same rotation speed, or different rotation speeds can be utilized. It is noted that the J.A. Woollam CO. Rotating Compensator Ellipsometer uses a "Stepper Motor" to cause Compensator rotation, and a common signal synchronizes both the Compensator and Detector. An alternative technique is to use a signal derived from the motor to synchronize the detector means. It is further noted that fixing the Polarizer Means (P) and Analyzer Means (A) in use provides another benefit in that polarization state sensitivity to input and output optics during data acquisition is essentially non-existent. This allows use of Optic Fibers, Mirrors, Beam Splitters, Lenses etc. for input/output.

Figure 1B:
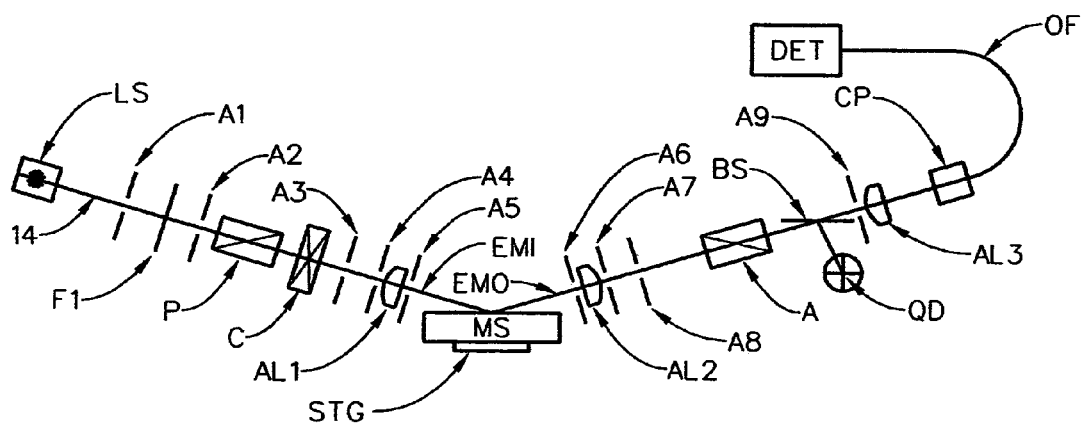
FIG. 1b shows the components of a Reflectance Mode, Material System Investigation Systems which has five apertures in the pathway of an electromagnetic beam prior to a material system, and four thereafter.

For insight, FIG. 1b is included to show a preferred polychromatic rotating compensator material system investigation system comprising a source (LS) of polychromatic beam (14) of electromagnetic radiation, a first aperture (A1), a second aperture (A2), a fixed polarizer (P), a rotating compensator (C), a third aperture (A3), a forth aperture (A4), a first substantially achromatic lens (AL1), a fifth aperture (A5), a stage (STG) for supporting a material system, a sixth aperture (A6), a second substantially achromatic lens (AL2), a seventh aperture (A7), an eighth aperture (A8), a fixed analyzer (A), a ninth aperture (A9), a third substantially achromatic lens (AL3), an optical fiber (OF)

and a detector means (DET) which contains a dispersive element and a multiplicity of detector means elements, there further being a UV filter (F1) present between said source (LS) of polychromatic beam of electromagnetic radiation and said stage (STG) for supporting a material system. When said polychromatic rotating compensator material system investigation system is used to investigate a material system (MS) present on said stage (STG) for supporting a material system, said fixed analyzer (A) and fixed polarizer (P) are maintained essentially fixed in position and said rotating compensator (C) is caused to continuously rotate while a polychromatic beam of electromagnetic radiation produced by said source (LS) of a polychromatic beam of electromagnetic radiation is sequentially caused to pass through said first aperture (A1), second aperture (A2), fixed polarizer (P), rotating compensator (C), third aperture (A3), forth aperture (A4), first substantially achromatic lens (AL1), fifth aperture (A5), said polychromatic beam of electromagnetic radiation also passing through said UV filter, then interact with a material system (MS) placed on said stage (STG) for supporting a material system (MS), then sequentially pass through said sixth (A6) aperture, second substantially achromatic lens (AL2), seventh aperture (A7), eighth aperture (A8), fixed analyzer (A), ninth aperture (A9), third substantially achromatic lens (AL3), enter said optical fiber (OF) and therevia enter said detector means (DET).

It is also mentioned that in the following it will be generally assumed that a Material System (MS) under investigation by a Spectroscopic Rotating Compensator Material System Investigation System is positioned upon the Material System Supporting Stage (STG). This need not be the case, as is described in U.S. Pat. No. 5,706,087 wherein a Material System (Sample), (MS) can be positioned in a Magneto-optic System which is physically too large to be supported by said Material System Supporting Stage (STG), or in an environmental control chamber. Further, especially where Ultraviolet range wavelengths are utilized, the system of FIG. 1a or 1b can be placed into an evacuated or purged, (eg. by nitrogen or argon), Chamber to the end that UV absorbing Oxygen and Water Vapor are not present therewithin. The entire FIG. 1a or 1b system can be so encompassed within a said Chamber, or only the Sample (MS) Stage portion thereof. The Chamber, where utilized, can be of multiple region construction.

Again, FIGS. 1a and 1b are included as demonstrative systems which can be applied to practice of the disclosed invention. The method of the disclosed invention involves obtaining data using such systems as a function of an independent variable, (eg. energy or wavelength), and mathematically fitting the data such that a plot of said mathematical function(s) is positioned substantially centrally in said data over a range of said independent variable. The preferred approach to evaluating parameters in the mathematical function is regression, (eg. least square).

Figure 2A:
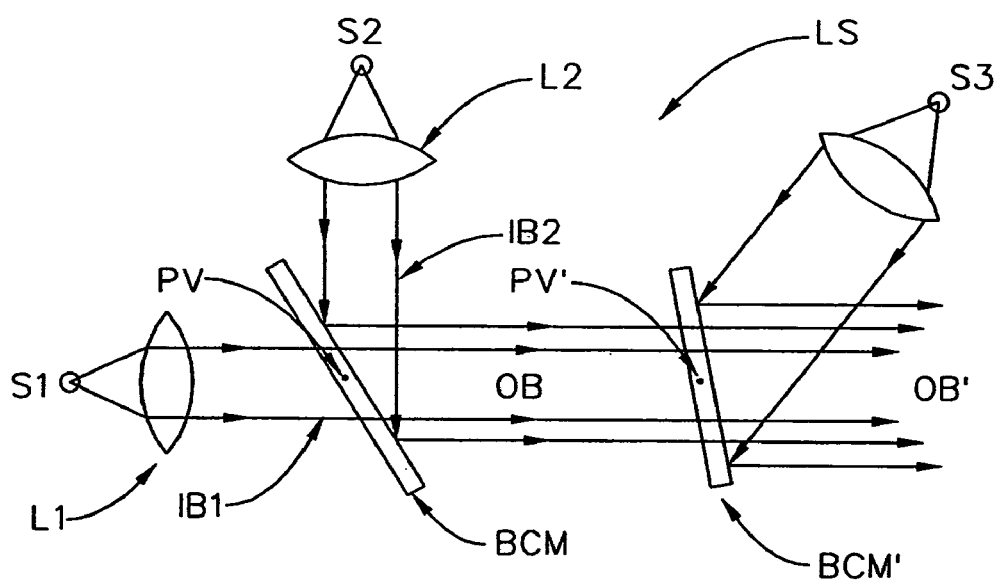
FIG. 2a shows a present invention system for providing an output beam (OB) or (OB') of polychromatic electromagnetic radiation which has a relatively broad and flattened intensity vs. wavelength characteristic over a wavelength spectrum.

Turning now to FIG. 2a, it is shown that the present invention system for providing an output beam (OB) of polychromatic electromagnetic radiation which has a relatively broad and flattened intensity vs. wavelength characteristic over a wavelength spectrum (generally identified as (LS)), said output beam (OB) of polychromatic electromagnetic radiation substantially being a comingled composite of a plurality of input beams, ((IB1) and (IB2)), of polychromatic electromagnetic radiation which individually do not provide as relatively broad and flattened an intensity vs. wavelength characteristic over said wavelength spectrum, as does said output comingled composite beam of polychromatic electromagnetic radiation, comprises:

a. at least a first (S1) and a second (S2) source of polychromatic electromagnetic radiation, ((IB1) and (IB2) respectively); and b. at least one electromagnetic beam combining (BCM) means.

The at least one electromagnetic beam combining means (BCM) is positioned with respect to said first (S1) and second (S2) sources of polychromatic electromagnetic radiation, ((IB1) and (IB2) respectively), such that a beam of polychromatic electromagnetic radiation (IB1) from said first (S1) source of polychromatic electromagnetic radiation passes through said at least one electromagnetic beam combining means (BCM), and such that a beam of polychromatic electromagnetic radiation (IB2) from said second (S2) source of polychromatic electromagnetic radiation reflects from said at least one electromagnetic beam combining means (BCM) and is comingled with said beam of polychromatic electromagnetic radiation (IB1) from said first source (S1) of polychromatic electromagnetic radiation which passes through said at least one electromagnetic beam combining means (BCM) along a common locus. The resultant beam of polychromatic electromagnetic radiation (OB) is substantially said output beam of polychromatic electromagnetic radiation which has a relatively broad and flattened intensity vs. wavelength over a wavelength spectrum, and comprises said comingled composite of a plurality of input beams of polychromatic electromagnetic radiation which individually do not provide such a relatively broad and flattened intensity vs. wavelength over a wavelength spectrum characteristic. Also shown in FIG. 2a are collimating lenses (L1) and (L2) to provide collimated electromagnetic radiation to the electromagnetic beam combining means (BCM), from first (S1) and a second (S2) source of polychromatic electromagnetic radiation, ((IB1) and (IB2) respectively).

Further shown in FIG. 2a is an optional third source of polychromatic electromagnetic radiation (S3) and a second electromagnetic beam combining means (BCM'). Said second electromagnetic beam combining means (BCM') is positioned with respect to said comingled beam of polychromatic electromagnetic radiation (OB), (which has a relatively broad and flattened intensity vs. wavelength over a wavelength spectrum, comprising wavelengths from sources (S1) and (S2), which exits said at least a first electromagnetic beam combining means (BCM)) such that said comingled beam of polychromatic electromagnetic radiation (OB) passes through said second electromagnetic beam combining means (BCM). Said second electromagnetic beam combining means (BCM) is further positioned with respect to said third source of polychromatic electromagnetic radiation (S3) such that a beam of electromagnetic radiation from said third source of polychromatic electromagnetic radiation (S3) reflects from said second electromagnetic beam combining means (BCM) to form a second resultant beam of polychromatic electromagnetic radiation (OB') which is substantially an output beam of polychromatic electromagnetic radiation having an even more relatively broadened and flattened intensity vs. wavelength over a wavelength spectrum comprising said comingled composite of a plurality of input beams of polychromatic electromagnetic radiation, (from sources (Si), (S2) and (S3)) projected along a common locus. It is emphasized that the sources (S1), (S2) and (S3) individually do not provide such an even more relatively broadened and flattened intensity vs.

wavelength over a wavelength spectrum characteristic and thereby is demonstrated the utility of the present invention.

A system as shown in FIG. 2a preferably include a pivot(s) (PV) (PV') to allow the beam combining means (BCM) and/or (BCM'), respectively, to be rotated. A direct application of the use of pivot(s) (PV), particularly where two degrees of rotational freedom are allowed thereby, is to allow making beam combining means transmitted and reflected electromagnetic beam components coincident in output beams (OB) and (OB'). Where sources of electromagnetic beams (S2) and (S3) can be moved, pivot(s) (PV) can also be beneficially applied to allow selection of an optimum angle at which a beam of electromagnetic radiation is caused to reflect from a beam combining means in use. The reason this might be desirable is that the angle at which a beam of electromagnetic radiation approaches a beam combining means affects the percent of an impinging beam which actually reflects therefrom and becomes part of the output beam (OB).

Figure 2B:
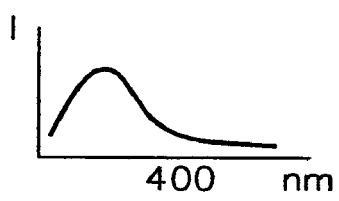
FIG. 2b demonstrates a spectrum of a polychromatic electromagnetic radiation (IB1) from said first source (S1) of polychromatic electromagnetic radiation which passes through said at least one electromagnetic beam combining means (BCM).
Figure 2C:
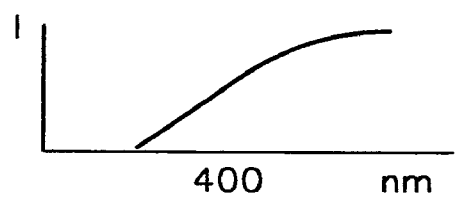
FIG. 2c demonstrates a beam of polychromatic electromagnetic radiation (IB2) from said second (S2) source of polychromatic electromagnetic radiation reflects from said at least one electromagnetic beam combining means (BCM).
Figure 2D:
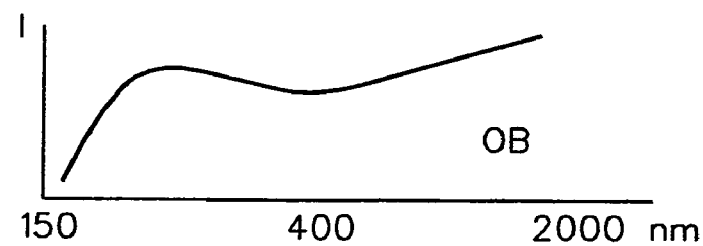
FIG. 2d demonstrates a resultant beam of polychromatic electromagnetic radiation (OB) which is substantially a comingled composite of a plurality of input beams (IB1) and (IB2) of polychromatic electromagnetic radiation which individually do not provide such a relatively broad and flattened intensity vs. wavelength over a wavelength spectrum characteristic as demonstrated in FIGS. 2b and 2c.

FIG. 2b demonstrates a spectrum of a polychromatic electromagnetic radiation (IB1) from said first source (S1) of polychromatic electromagnetic radiation which passes through said at least one electromagnetic beam combining means (BCM). FIG. 2c demonstrates a beam of polychromatic electromagnetic radiation (IB2) from said second (S2) source of polychromatic electromagnetic radiation reflects from said at least one electromagnetic beam combining means (BCM). FIG. 2d demonstrates a resultant beam of polychromatic electromagnetic radiation (OB) which is substantially a comingled composite of a plurality of input beams (IB1) and (IB2) of polychromatic electromagnetic radiation which individually do not provide such a relatively broad and flattened intensity vs. wavelength over a wavelength spectrum characteristic as demonstrated in FIGS. 2b and 2c.

Figure 3A:
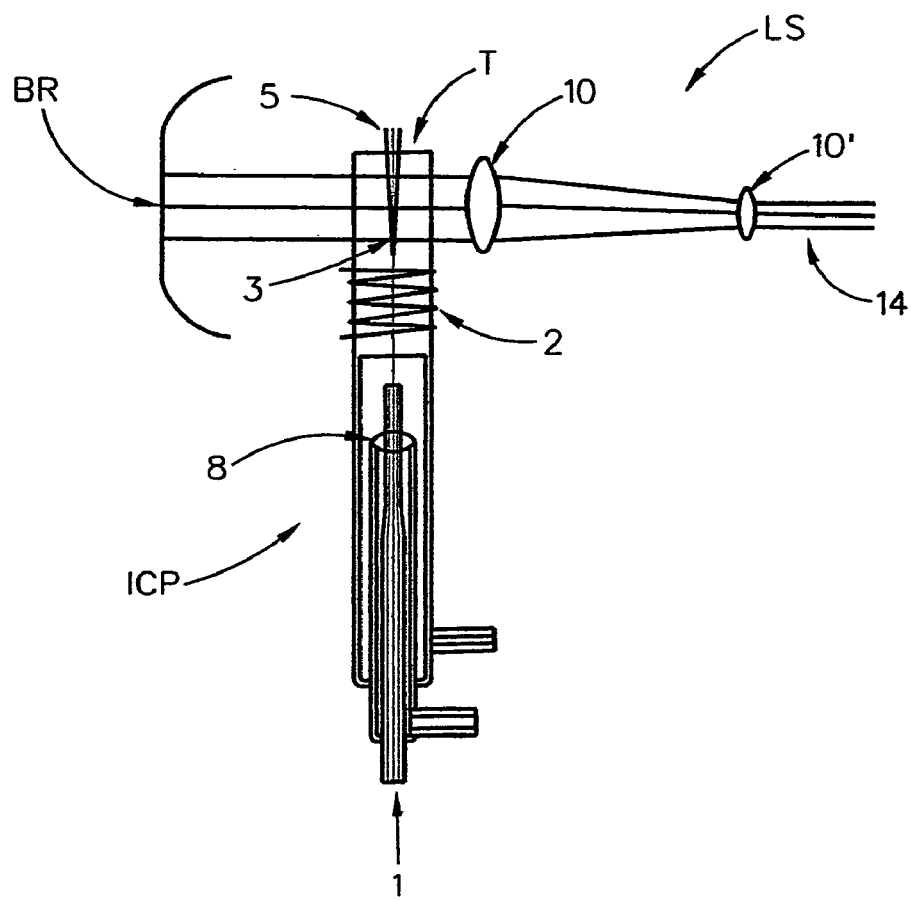
FIG. 3a shows a Plasma Source of Spectroscopic Electromagnetic Radiation.

FIG. 3a shows an Inductively Coupled Plasma system comprising means for injecting a flow of carrier gas (8) into a region of a Tube (T) circumscribed by a Means for providing Electrical Excitation (2), shown to typically be a coil to which can be applied Electrical Energy of an appropriate Frequency. Also present are means for injecting an Analyte containing flow (1) into the region of the Tube (T) which is circumscribed by said Means for providing Electrical Excitation (2). In use the Analyte can be, (but need not be if the relaxing excited carrier gas atoms per se. provide desired wavelengths), injected into the region of the Tube (T) which is circumscribed by said Means for providing Electrical Excitation (2) and Electrical Energy is applied thereto. The result is that a spectrum of wavelengths are emitted from the Tube (T). Excited atoms are produced in the location represented by (3), and First Lens (10) is positioned to collect some portion of said Spectrum of Wavelengths which result as the excited Atoms relax. First Lens (10) directs said wavelengths as shown. A Second Lens (10') can be applied to collimate the results and provide a Beam of Electromagnetic Radiation (14). Note that said Lenses (10) (10') can be positioned to collect wavelengths from relaxing Metastable atoms. See FIGS. 1 and 2 to identify how Beam (14) is positioned prior to a Polarizer (P) in the Systems thereof. It should be appreciated that the shown Plasma Beam (5) is directed so as not to impinge upon lens (10). Note the presence of a Back Reflector (BR) which can be applied to increase the Intensity of the Beam of Electromagnetic Radiation (14) by redirecting Electromagnetic Radiation emitted in the opposite direction. Back Reflectors can also be effective reducing Lines in an emitted Spectra, and depending on surface characteristics, Back Reflectors (BR) can serve to emphasize certain wavelength ranges and de-emphasize others, (eg. emphasize IR and UV and de-emphasize the Visible. A more uniform Spectra in Beam (4) can then be achieved by, for instance, using a Silicon base and coating the surface thereof with Silicon Dioxide, or applying one or multiple layers to a Back Reflector Surface wherein the base and one or more layers are any functional combination. (Note the Back Reflector (BR) is not shown in proper geometric shape and orientation, but is rather presented to disclose the function it can perform).

Figure 3B:
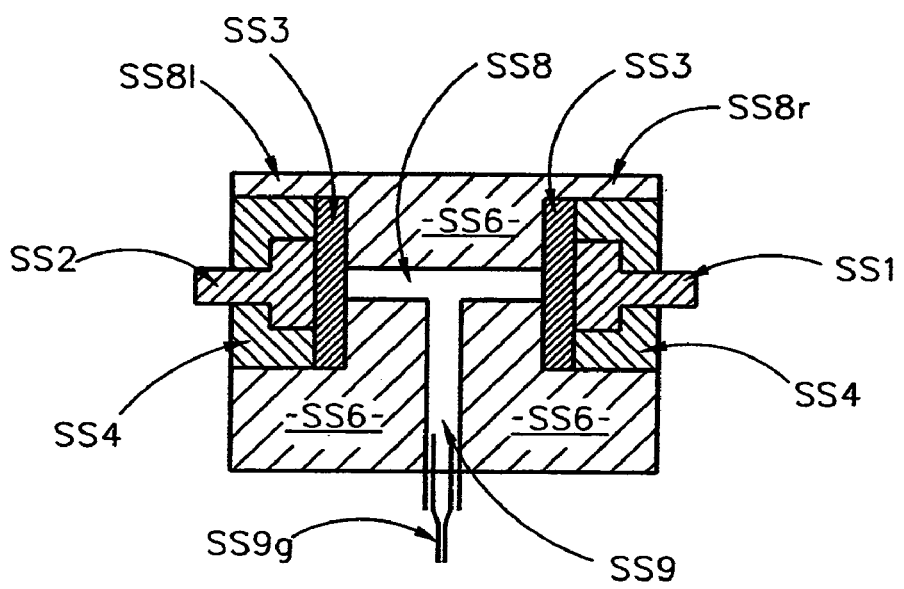
FIG. 3b shows another plasma based source of electromagnetic radiation.

FIG. 3b shows another plasma based source of electromagnetic radiation which can be customized to provide desired wavelength content (SS10). Shown are a containing block of machinable material, such as Magnesium or Lithium Fluoride (SS6), with Electrodes (SS1) and (SS2) which are protected by Disks (SS3) and Sealing Means (SS4). First Hole (SS8) and Second Hole (SS9) are shown, along with a Gas Entering Tube (SS9g). During use a selected gas such a Argon, Krypton or Xenon is entered via Tube (SS9g) into First Hole (SS8) via Second Hole (SS9) to an appropriate pressure. Next, Electrical Energy is applied across Electrodes (SS1) and (SS2). Electromagnetic Radiation is emitted as a result in a substantially spherical pattern, except where blocked by said Electrodes (SS1) and (SS2).

Figure 4A:
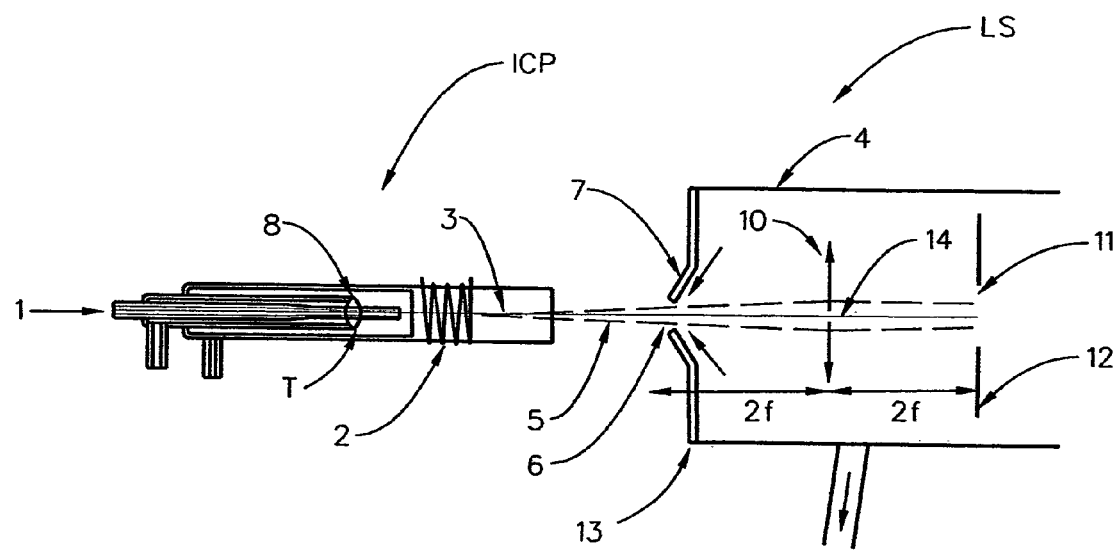
FIGS. 4a and 4b show Plasma Source of Spectroscopic Electromagnetic Radiation as disclosed in Japanese Abstract 2003-307491 which was published 31 Oct. 2003 based upon Japanese Application 2003-048215, filed 21 Jan. 2003.
Figure 4B:
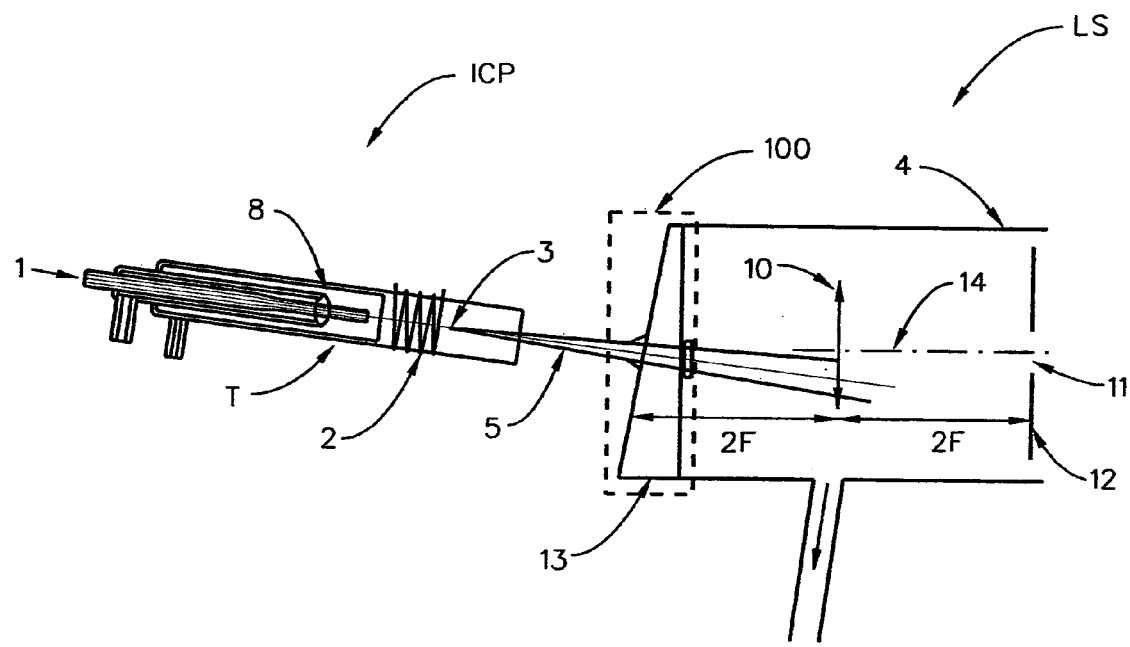

FIGS. 4a and 4b show alternative embodiments of the Source of Electromagnetic Radiation (LS) and are gleened from Japanese Application 2003-048215. It is first noted that the configuration in FIG. 4a is similar to an Inductively Coupled Plasma System which is coupled to a Mass Spectrometer System such that particles charged by the Means for providing Electrical Excitation (2) are entered to the Mass Spectrometer (4) via what is typically termed a Skimmer (7). Note that the Means for providing Electrical Excitation (2) has a Central Axis (3) whereat is produced a plasma. Using the descriptive language of the Japanese Application 2003-048215, also shown is an extraction Enclosure (4) which receives a Beam Comprised of ions and atoms and/or Electrons (5) derived from the Plasma. Also shown is an optical Lens (10) which collects luminous radiation emitted from the Beam (5). In FIG. 4b said lens is not exposed directly to said Plasma produced along Central Axis (3). Also shown is a Sighting Device (100) comprising a Metallic Structure (13) which is Substantially Cylindrical Input Aperture for Analysis of Beam (5). Note that in FIG. 3a lens (10) intercepts Electromagnetic Radiation from emitted from and directs it as a Beam of Electromagnetic Radiation (14). Again see FIGS. 1 and 2 for the location of said Beam of Electromagnetic Radiation (14) in the present invention.

Figure 5A:
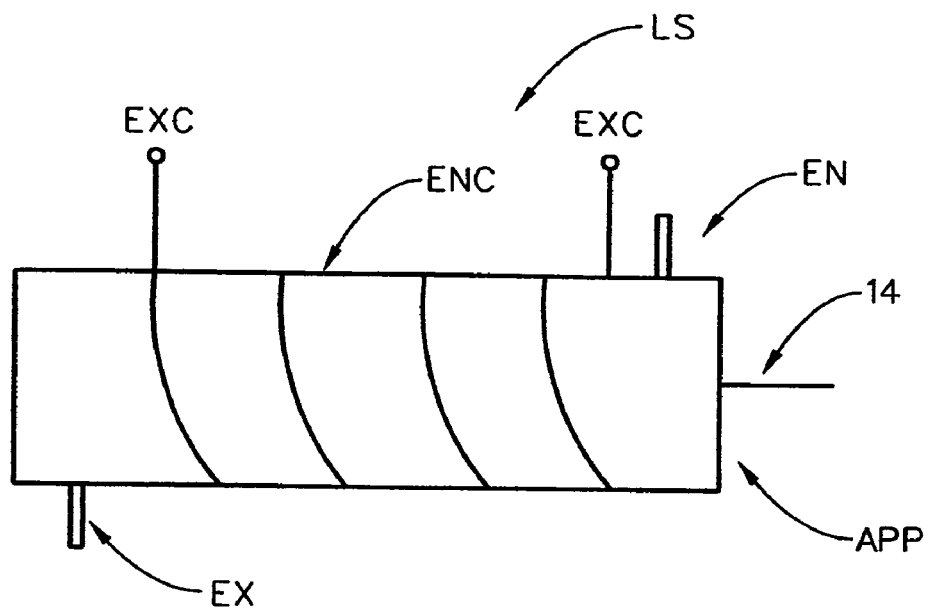
FIGS. 5a and 5b demonstrate axially viewed plasma sources.
Figure 5B:
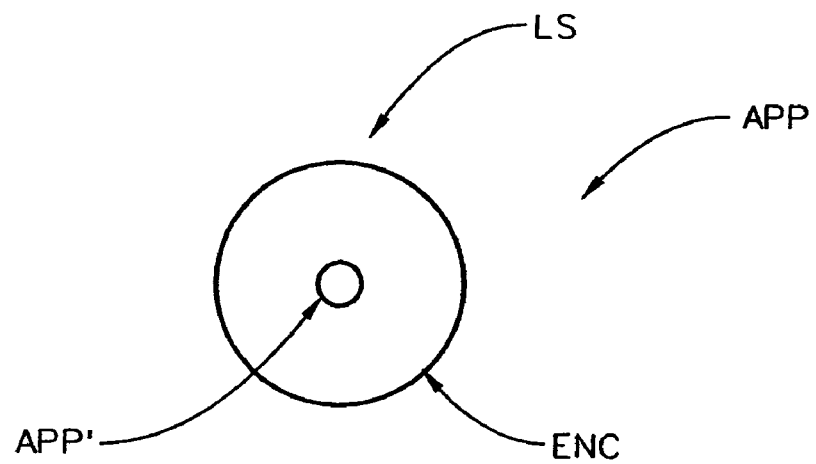

FIGS. 5a and 5b demonstrate axially viewed plasma sources. Shown is an Enclosure (ENC) comprising means for Entering (EN) and Exiting (EX) Gas and Analyte thereinto and therefrom. Also shown is a Coil with ends accessible for applying Plasma generating Electromagnetic Excitation (EXC). FIG. 5b shows that when viewed from an end, from a sufficient distance away, said Source appears to be a Point Source. Indicated are (APP) and (APP'). (APP) is simply the entire cross section, and (APP') indicates a smaller cross-section which can result from containing the formed Plasma via application of Magnetic Fields. For insight, it is noted that even the Sun appears to be a Point Source when viewed from 93 Million Miles away, hence, the effect demonstrated by (APP) and (APP') only determines the distance it must be removed from the Polarizer (P) in FIGS. 1 and 2.

It should be appreciated that in any embodiment, the wavelength content of the Beam of Electromagnetic Radiation (14) can be controlled by what Analyte(s) are present in the Analyte containing flow (1), in combination with any effects of the Carrier Gas (8) composition.

Figure 6A:
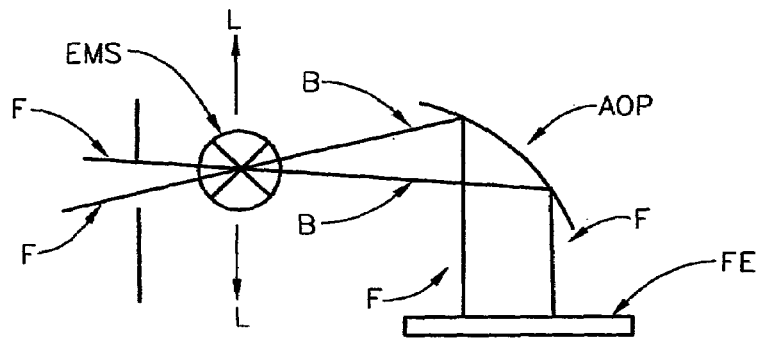
FIG. 6a shows a back-reflector system comprising an off-axis parabolic (OAP) back-reflector to a flat reflector.
Figure 6B:
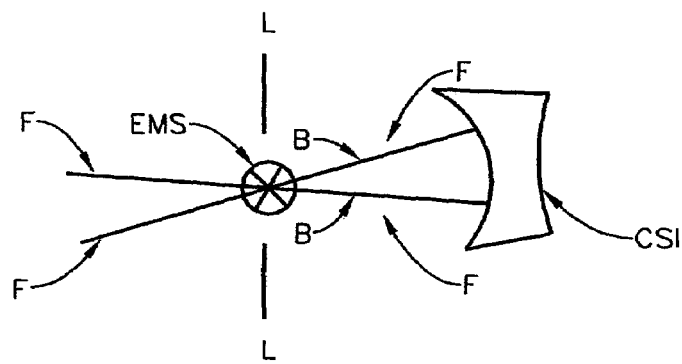
FIG. 6b demonstrates a concave backreflector (CSI).
Figure 6C:
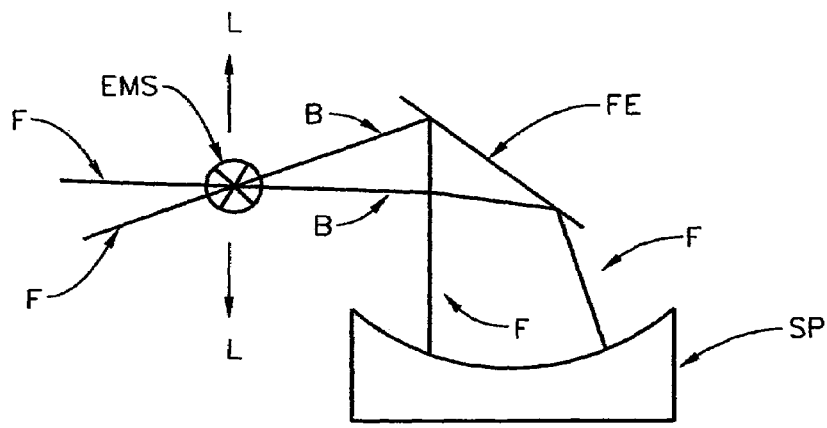
FIG. 6c shows a back-reflector comprising a flat mirror (FE) and a spherical mirror (SP).

The disclosed invention also provides improved reflecting means for application in redirecting backside electromagnetic radiation emitted by a source (EMS) thereof. FIG. 6a shows a Source (EMS) of electromagnetic radiation and a first reflecting means comprised of an Off-Axis Parabolic Mirror (OAP) and a Flat Reflecting Element (FE), in that sequential order. FIG. 6b shows a Source (EMS) of electromagnetic radiation, and a second reflecting means comprising a Concave Si Mirror (CSI), which can have a thin film of Oxide or other material thereupon, to effect different reflection efficiencies at different-wavelengths. FIG. 6c shows a Source (EMS) of electromagnetic radiation and third reflecting means comprising a Flat Reflecting Element (FE) and a spherical mirror (SP), in that sequential order.

In all three cited examples, note that electromagnetic radiation emits from the Source thereof (EMS) in a "Forward" (F) direction, and in a "Backward" (B) direction. Note The radiation emitted in the "Backward" direction (B) is, in each of the FIGS. 6a, 6b and 6c examples redirected toward the "Forward" (F) direction. Radiation identified as (L) is lost, but could, for instance, be focused onto a light fiber and directed for application in sample alignment.

It is also mentioned that some or all of the reflecting means can be affixed to adjustment means to enable directing an electromagnetic beam in an optimum manner.

It should be appreciated that the Material, (eg. Silicon, possibly with a thin layer of Oxide or other materials thereupon), serves to reflect different wavelengths with different efficiency. For instance, Si with a 600 A film of SiO2 has been found to reflect UV and IR wavelengths more efficiently than Visible Wavelengths. This leads to a more uniform Intensity vs. Wavelength Spectrum in the beam directed in the "Forward" direction.

Figure 6D:
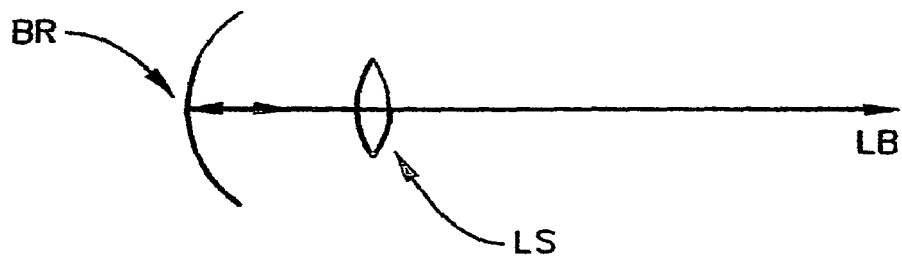
FIG. 6d shows a Source (LS) of Electromagnetic Radiation, and a Back-Reflector (BR) positioned to redirect electromagnetic radiation emitted opposite to the direction of a Beam (LB) thereof, into the direction of a beam (LB) thereof.
Figure 6E:
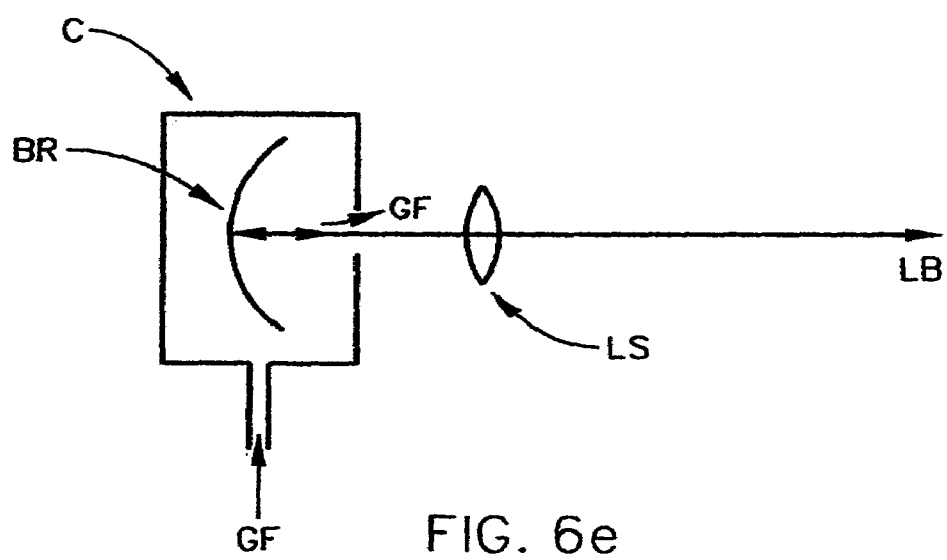
FIG. 6e shows the Back-Reflector (BR) of FIG. 1 in a Container (C) which allows for the flow of Gas (GF) into and out thereof.
Figure 6F:
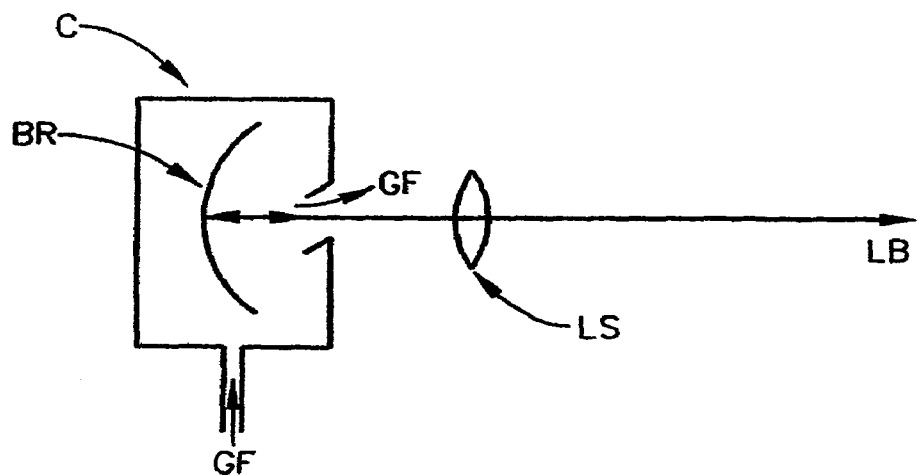
FIG. 6f is a variation of FIG. 6a, and shows that the Gas Flow (GF) out of the Container (C) can be directed away from the Source (LS) of Electromagnetic Radiation.

Turning now to FIG. 6d, there is shown a Source (LS) of Electromagnetic Radiation, and a Back-Reflector (BR) positioned to redirect electromagnetic radiation emitted opposite to the direction of a Beam (LB) thereof, into the direction of a beam (LB) thereof. FIG. 6e shows the Back-Reflector (BR) of FIG. 6d in a Box (B) which allows for the flow of Gas (GF) into and out thereof. FIG. 6f is a variation of FIG. 6e, wherein the Gas Flow (GF) out of the Container (C) is directed away from the Source (LS) of Electromagnetic Radiation. This has been found beneficial because it avoids detrimental cooling of the Source (S).

Figure 7A:
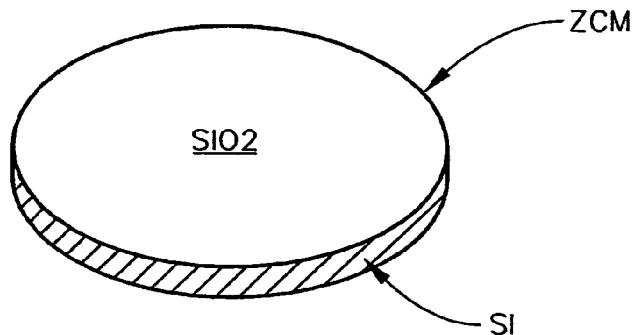
FIGS. 7a, 7b and 7c demonstrate use of a reflecting means (ZCM) to change relative intensities of reflected electromagnetic radiation (EMO) as compared to incident electromagnetic radiation (EMI).
Figure 7B:
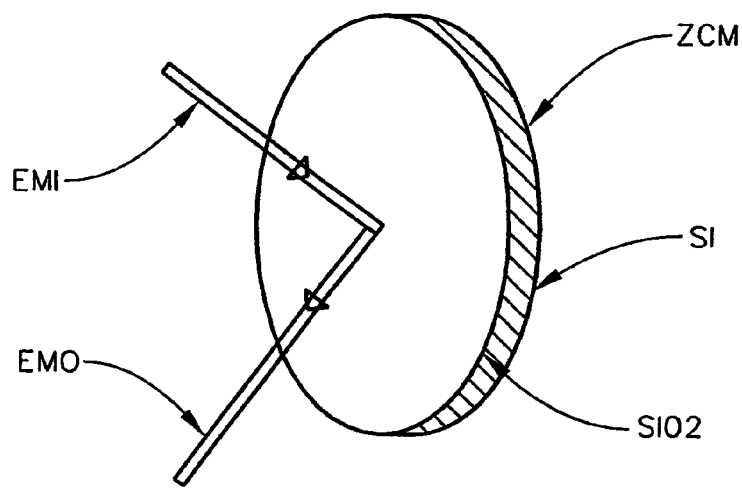
Figure 7G:
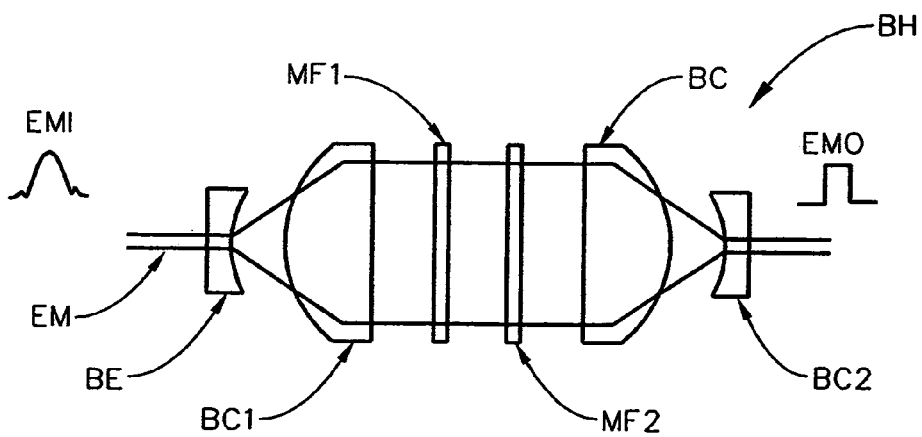
FIG. 7g shows a system for radially homogenizing the energy content of a beam of electromagnetic radiation.
Figure 7C:
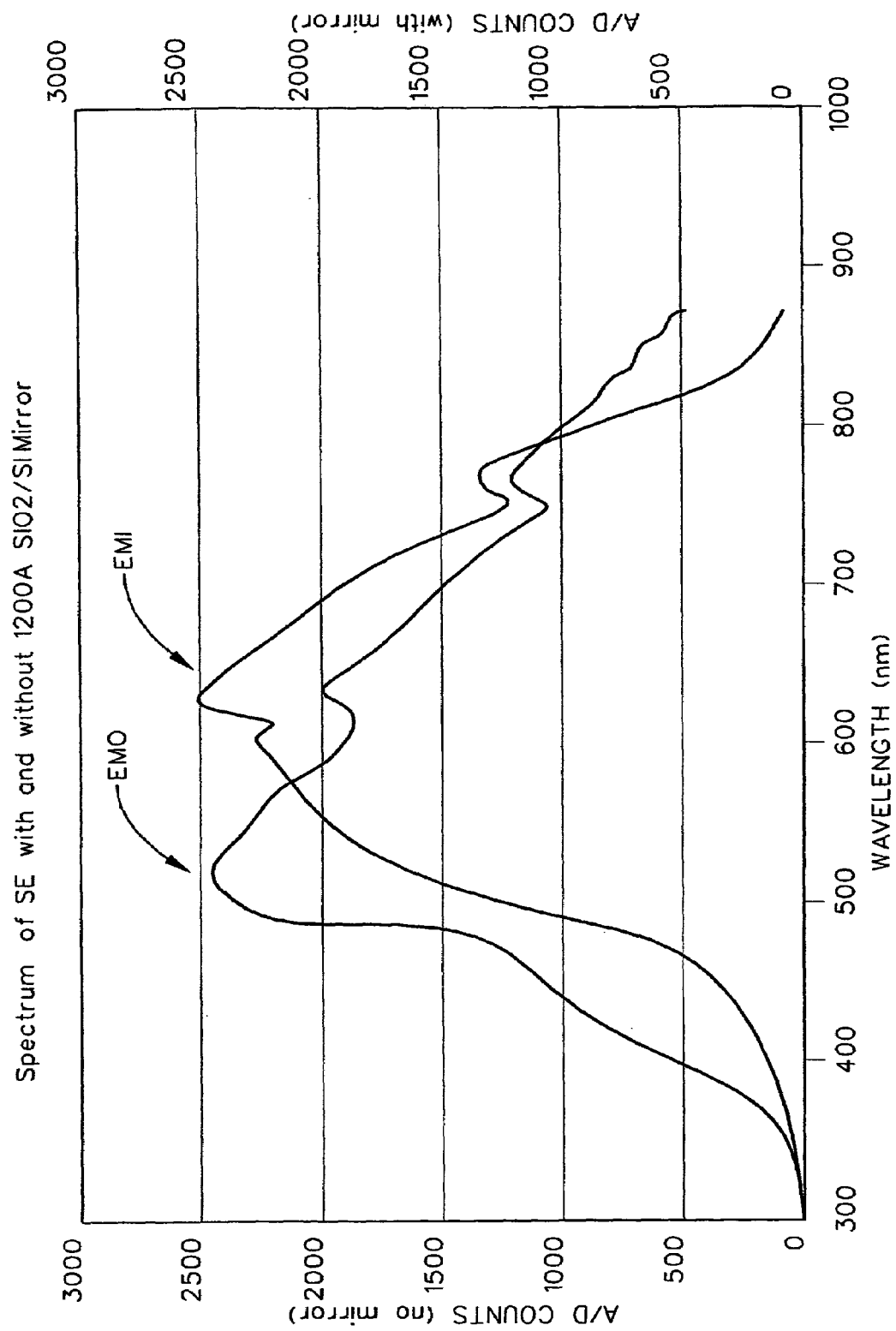
Figure 7D:
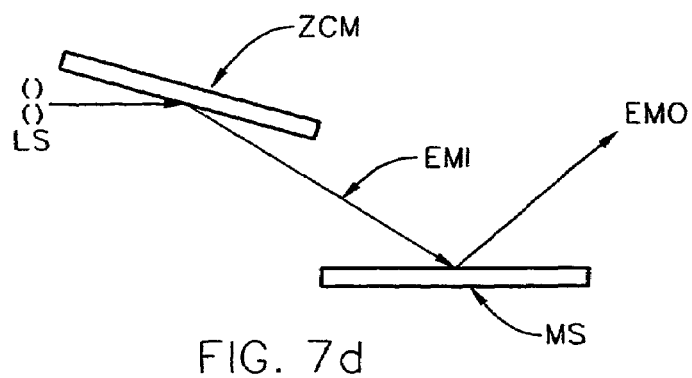
FIG. 7d demonstrates a possible placement of the reflecting means (ZCM) between a Source (LS) of electromagnetic radiation and a Sample (MS).

FIGS. 7a, 7b and 7c demonstrate use of a reflecting means to change relative intensities of electromagnetic radiation caused to impinge thereupon. Shown in FIG. 7a is a Silicon Wafer with Silicon Dioxide ($SiO_2$) on the surface thereof, as a composite identified as (ZCM). FIG. 7b shows Incident (EMI) and Reflected (EMO) electromagnetic radiation and FIG. 7c shows how the relative intensities of (EMI) and (EMO) are changed by the FIG. 7b interaction with (ZCM). Note that shorter and longer wavelength intensities are enhanced. FIG. 7d demonstrates one approach to application of (ZCM) to direct beam (EMI).

Figure 7E:
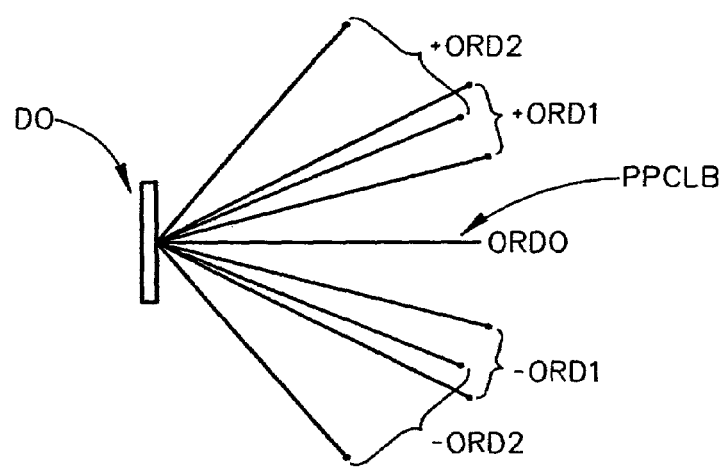
FIGS. 7e and 7f demonstrate use of a Dispersive Optics (DO) and Order Filtering (F1).
Figure 7F:
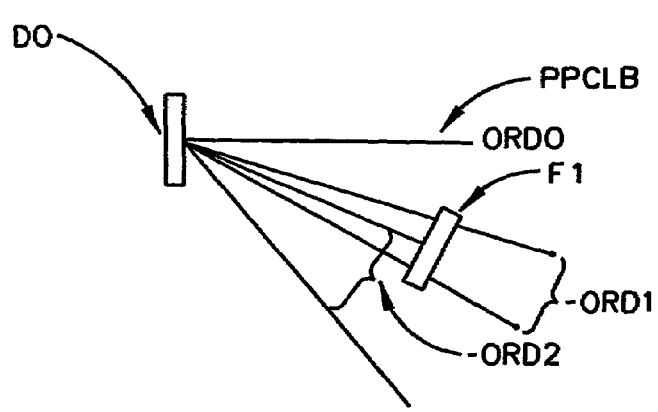

FIGS. 7e and 7f demonstrate use of a Dispersive Optics (DO) and Order Filtering (F1). FIG. 7e shows use of Dispersive Optics, (eg. a grating), to distribute wavelengths into multiple Orders (eg. +ORD1, +ORD2, ORD0, −ORD1 and −ORD2), based on an the wavelength content of an incident Polychromatic Polarized Colliminated Beam (PP-CLB) of Electromagnetism. FIG. 7f shows Filtering (F1) to de-emphasize wavelengths present in −ORD2.

FIG. 7g shows a system (BH) for radially homogenizing the energy content of a beam of electromagnetic radiation (EMI). Shown are a Beam Expander (BE), a Beam Colliminating Lens (BC1), two Multi-Facet Elements (MF1) (MF2), a Beam Focusing Lens (BC) and a Second Beam Colliminating Lens (BC2). Note the shape of (EMO).

Continuing, to focuse electromagnetic radiation onto small spots on samples, (eg. 35 microns), the present invention can make use of custom multiple element lenses in which cavities are filled with liquid. FIG. 8a shows a One (8a) Cavity System. FIGS. 8b and 8c show Two and Three Cavity systems. FIGS. 8d, 8e, 8f and 8g demonstrate that a Cavity can be of various flat, concave, convex shapes at interfaces between effective elements and cavity boundaries. Any lens with at least one flowable material filled cavity is within the scope of the disclosed invention.

Figure 9A:
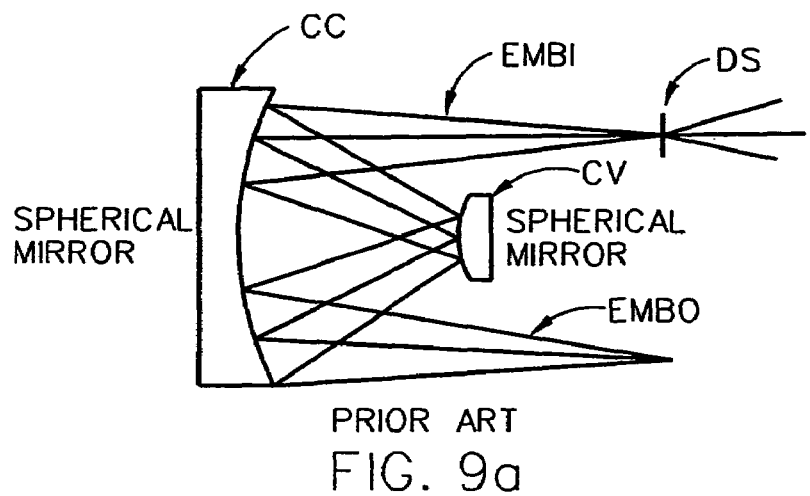
FIG. 9a demonstrates a Prior art (eg. expired U.S. Pat. No. 3,748,015 to Offner), 1:1 imaging System.

FIG. 9a demonstrates a Prior art (eg. U.S. Pat. No. 3,748,015 to Offner), System. Note that a Point Source (PS) provides Input Electromagnetic Beam (EMB1) to reflect from Concave Spherical Mirror (CC) at a first location thereon onto Concave Spherical Mirror and again from reflect from Concave Spherical Mirror (CC) at a second location thereon so as to Image the Point Source. If Colliminated Electromagnetic Radiation were input Colliminated Electromagnetic Radiation would be output.

Figure 9B:
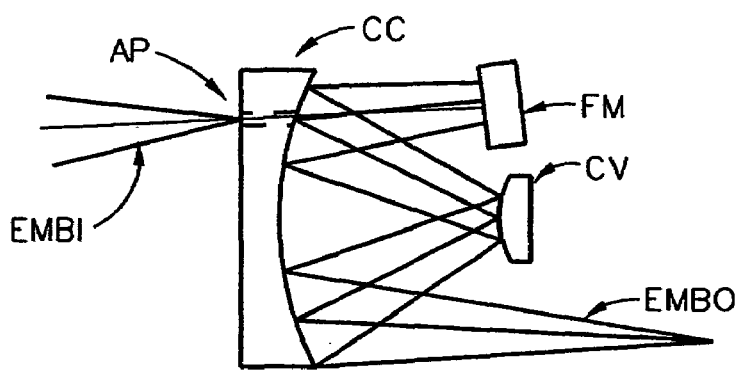

FIG. 9b demonstrates one embodiment of the disclosed invention is a combined spatial filter and imaging system comprising three elements:

a) a concave spherical mirror (CC) having at least one concave spherical surface and an aperture hole (AP') therethrough;

b) a flat mirror (FM); and c) a convex spherical mirror (CV) having at least one convex spherical surface.

Said elements are arranged such that electromagnetic radiation (EMBI) caused to approach the concave spherical mirror (CC) passes through said aperture hole (AP') and reflects from said flat mirror (FM) onto a first location of a concave surface of said concave spherical mirror (CC). It then reflects from said first location onto a convex spherical surface of said convex spherical mirror (CV) and reflects therefrom onto a second location of said concave surface of said concave spherical mirror (CC) as a converging beam of electromagnetic radiation (EMBO).

Figure 9C:
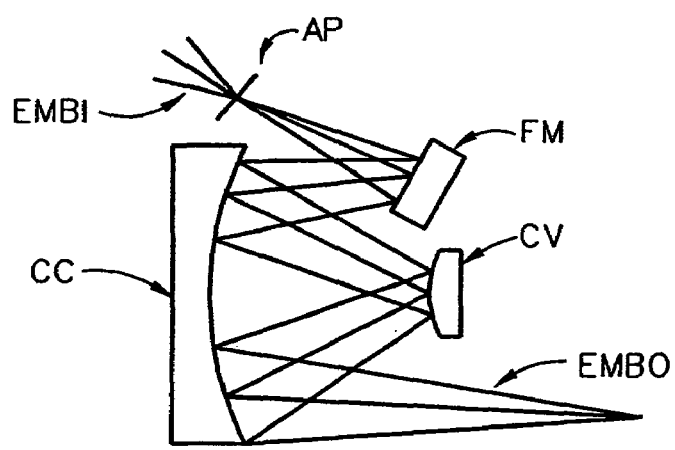

FIG. 9c demonstrates a second embodiment of the disclosed combined spatial filter and imaging system comprises:

a) an aperture (AP);

b) a flat mirror (FM);

c) a concave spherical mirror (CC) having at least one concave spherical surface; and d) a convex spherical mirror (CV) having at least one convex spherical surface.

Said elements are arranged such that electromagnetic radiation ((EMBI) which images said aperture (AP) is caused to approach the flat mirror (FM) and reflect therefrom onto a first location of a concave surface of said concave spherical mirror (CV). It then reflects from said first location onto a convex spherical surface of said convex spherical mirror (CV) and reflects therefrom onto a second location of said concave surface of said concave spherical mirror (CC) from which it reflects as a converging beam of electromagnetic radiation (EMBO).

FIG. 9d shows that Said embodiment can, in addition to a First Flat Mirror (FM1) include a Second Flat Mirror (FM2) positioned to intercept and reflect electromagnetic radiation reflected from said second location of said concave surface of said concave spherical mirror (CC) as a converging beam of electromagnetic radiation. (EMBO). Said modified second embodiment then comprises five elements:

a) an aperture (AP);
b) a first flat mirror (FM1);
c) a concave spherical mirror (CC) having at least one concave spherical surface;
d) a convex spherical mirror (CV) having at least one convex spherical surface; and
e) a second flat mirror (FM2).

Said elements are arranged such that electromagnetic radiation (EMBI) which images said aperture (AP) is caused to approach the first flat mirror (FM1) and reflect therefrom onto a first location of a concave surface of said concave spherical mirror (CC). It reflects from said first location onto a convex spherical surface of said convex spherical mirror (CV) and reflect therefrom onto a second location of said concave surface of said concave spherical mirror (CC) reflects therefrom onto said second flat mirror (FM2) which is positioned to intercept and reflect electromagnetic radiation reflected from said second location of said concave surface of said concave spherical mirror (CC) as a converging beam of electromagnetic radiation (EMBO).

FIGS. 9e and 9f demonstrate that in ellipsometry applications it is best to keep the angle of incidence of electromagnetic radiation onto a flat mirror low, (eg. less than 20 degrees). Where it is desired to use a larger angle, say 45 degrees, the presently disclosed invention can be advantageously modified. An example is a system for investigating a sample comprising:

a source of electromagnetic radiation (see (LS) in FIG. 1a);

an aperture (AP);

first (IMG1) and second (IMG2) imaging systems, each thereof comprising four elements:
a) a first flat mirror (FM1);
b) a concave spherical mirror (CC) having at least one concave spherical surface;
c) a convex spherical mirror (CV) having at least one convex spherical surface; and
d) a second flat mirror (FM2).

Said elements are arranged such that electromagnetic radiation (EMBI) is caused to approach the first flat mirror (FM1) and reflect therefrom onto a first location of a concave surface of said concave spherical mirror (CC), reflect from said first location onto a convex spherical surface of said convex spherical mirror (CV) and reflect therefrom onto a second location of said concave surface of said concave spherical mirror (CC) onto said second flat mirror (FM2) positioned to intercept and reflect electromagnetic radiation reflected from said second location of said concave surface of said concave spherical mirror (CC) as a converging beam of electromagnetic radiation (EMBO);

and a detector, (see (DET) in FIG. 1a);

said sample (S) being positioned between said first (IMG1) and second (IMG2) imaging systems.

Said first (IMG1) imaging system is positioned to image electromagnetic radiation from the source thereof as it passes through said aperture (AP) and direct it onto a surface of said sample (S) at an oblique angle of incidence, and said second (IMG2) imaging system is positioned to receive electromagnetic radiation reflected from the sample and pass it on to said detector. Note that the propagation direction of electromagnetic radiation entering and exiting each of said first and second imaging systems is substantially unchanged by passing therethrough. Said system is further characterized in that a plane formed by the locus of the electromagnetic radiation passing through the first (IMG1) imaging system is oriented 90 degrees to a plane formed by the locus of the electromagnetic radiation passing through the second (IMG2) imaging system, the purpose being to minimize effects of said first (IMG1) and second (IMG2) imaging systems on a polarization state of said electromagnetic radiation which passes through both thereof.

A modified system for investigating a sample comprises:

a source of electromagnetic radiation;

an aperture (AP);

first (IMG1) and second (IMG2) imaging systems, each thereof comprising four elements:
a) a first flat mirror (FM1);
b) a concave spherical mirror (CC) having at least one concave spherical surface;
c) a convex spherical mirror (CV) having at least one convex spherical surface; and
d) a second flat mirror (FM2);

said elements being arranged such that electromagnetic radiation is caused to approach the first flat mirror (FM1) and reflect therefrom onto a first location of a concave surface of said concave spherical mirror (CC), reflect from said first location onto a convex spherical surface of said convex spherical mirror (CV) and reflect therefrom onto a second location of said concave surface of said concave spherical mirror (CC) onto said second flat mirror (FM2) positioned to intercept and reflect electromagnetic radiation reflected from said second location of said concave surface of said concave spherical mirror (CC) as a converging beam of electromagnetic radiation;

and a detector;

said first (IMG1) and second (IMG2) imaging systems being positioned on the same side of the sample;

the propagation direction of electromagnetic radiation entering and exiting each of said first and second imaging systems being substantially unchanged by passing therethrough.

said system being further characterized in that a plane formed by the locus of the electromagnetic radiation passing through the first imaging system is oriented 90 degrees to a plane formed by the locus of the electromagnetic radiation passing through the second imaging system, the purpose being to minimize effects of said first and second imaging systems on a polarization state of said electromagnetic radiation which passes through both thereof.

As demonstrated by FIGS. 1a and 1b said system for investigating a sample can further comprises:
a) a polarizer (P) between said source (LS) and sample (S); and
b) an analyzer (A) between said sample (S) and detector (DET);

and constitute an ellipsometer, and if a compensator (C) (C') (C") is present between said source (LS) and detector (DET), a polarimeter results.

It is emphasized that the systems of FIGS. 9a-9f do not focus a beam of electromagnetic radiation, but IMAGE at their output whatever is input thereto. This is distinguishing over the 526 and 424 patents of KLA Tencor which were identified in the Background Section of this Specification.

Figure 10:
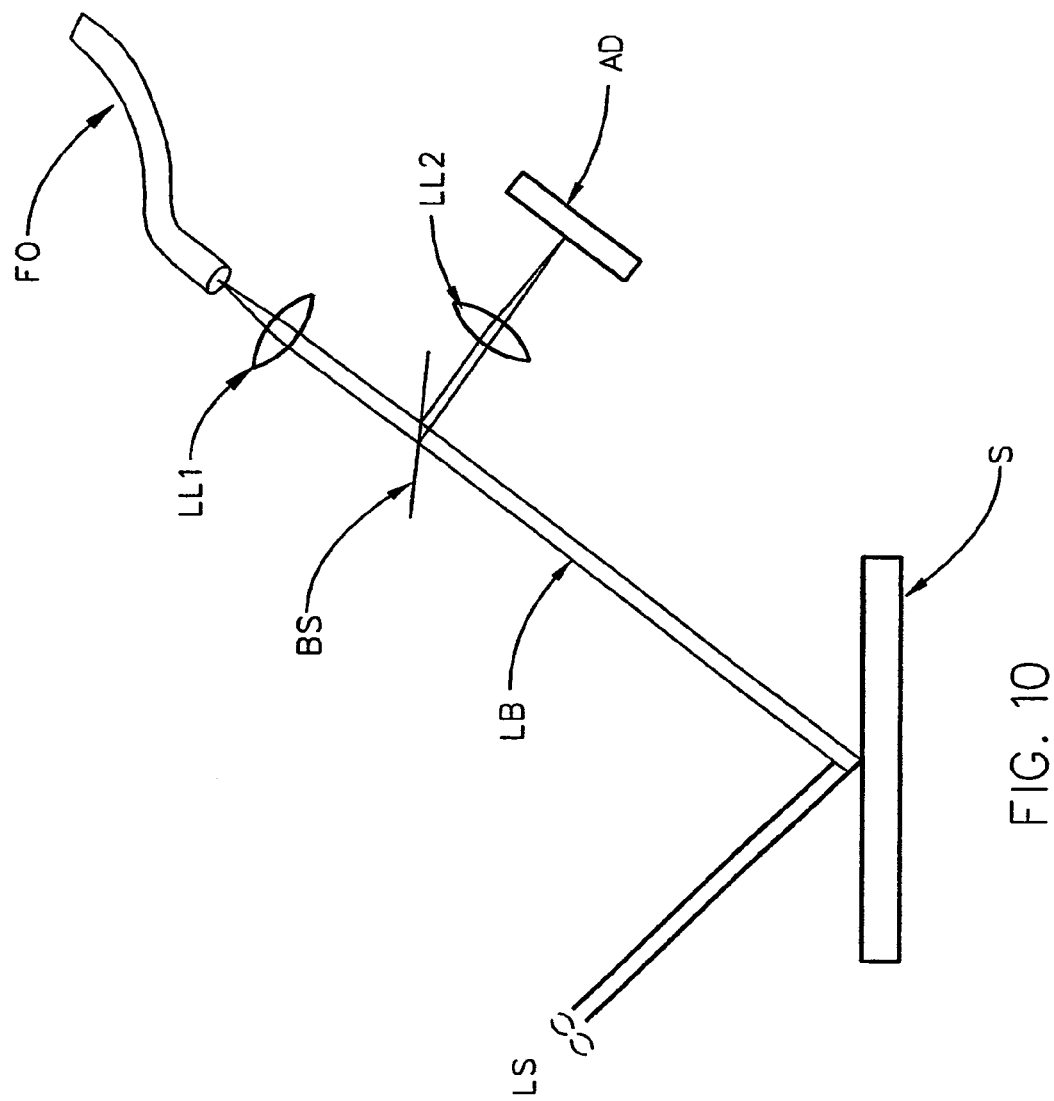
FIG. 10 shows a system for focusing a Beam of Electromagnetic Radiation (LB) which is originated at Source (LS) and is reflected from a sample (S) onto the input of a Fiber Optic (FO).

Continuing, FIG. 10 shows a system for focusing a Beam of Electromagnetic Radiation (LB) which is originated at Source (LS) and is reflected from a sample (S) onto the input of a Fiber Optic (FO). Shown are a Beam Splitter (BS) and Lenses (LL1) and (LL2) which focus said Beam (LB) onto the end of said Optical Fiber (OF) and an Alignment Detector, respectively. Signals developed by the Alignment Detector, (eg. a Quad Detector), can be used to keep the relatively small diameter Beam focused centrally onto the Fiber Optic (FO).

Figure 11:
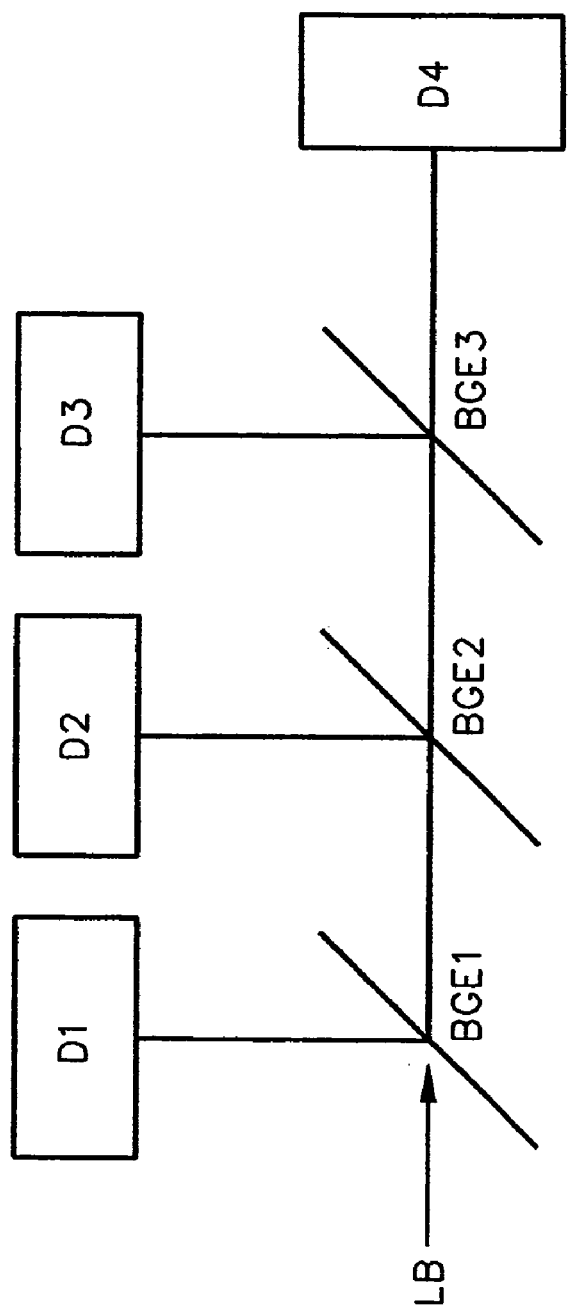
FIG. 11 shows a sequence of decreasing Bandgap Semiconductor elements oriented to direct reflected electromagnetic radiation into detectors.

FIG. 11 shows a Sequence of Decreasing Bandgap Semiconductor Elements (BGE1) (BGE2) (BGE3) oriented to direct reflected electromagnetic radiation into detectors (D1) (D2) (D3) respectively. The Beam of Electromagnetic Radiation (LB) shown entering Band Gap Element (BGE1) can be from an Optic Fiber, as shown in FIG. 10 to receive a Beam (LB) of Electromagnetic Radiation.

The terminology "material system investigation system" is, where applicable, used in the Claims to indicate any spectrophotometer, reflectometer, ellipsometer, polarimeter or the like systems.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for providing a beam of electromagnetic radiation comprising:
   a source of electromagnetic radiation; and
   at least one back-reflector having a reflective surface which reflects UV wavelengths more efficiently than visual range wavelengths;
   said at least one back-reflector being situated with respect to said source of electromagnetic radiation such that at least some electromagnetic radiation emitted in a direction other than that of the beam of electromagnetic radiation, is redirected into the direction of said beam of electromagnetic radiation thereby;
   said system further comprising provision for flowing gas over said back-reflector surface to prevent deposition of contaminants onto said back-reflector reflective surface.

2. A system for providing a beam of electromagnetic radiation comprising:
   a source of electromagnetic radiation; and
   at least one back-reflector having a reflective surface which reflects UV wavelengths more efficiently than visual range wavelengths;
   said at least one back-reflector being situated with respect to said source of electromagnetic radiation such that at least some electromagnetic radiation emitted in a direction other than that of the beam of electromagnetic radiation, is redirected into the direction of said beam of electromagnetic radiation thereby;
   said system being further characterized in that said at least one back-reflector is in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface.

3. An ellipsometer system comprising a source of electromagnetic radiation, a polarizer, a stage for supporting a sample, an analyzer and a detector, there optionally being at least one compensator present between said polarizer and stage and/or between said stage and analyzer;
   such than in use a beam of electromagnetism is caused to be directed by said source thereof toward a sample placed on said stage, interact with said sample, pass through said analyzer and enter said detector, said beam also passing through any present compensator;
   said source of electromagnetic radiation comprising at least one back-reflector having a reflective surface, said at least one back-reflector being situated in said source of electromagnetic radiation such that at least some electromagnetic radiation emitted in a direction other than that of the beam of electromagnetic radiation, is redirected into the direction of said beam of electromagnetic radiation thereby; said at least one back-reflector having a reflective surface which reflects UV wavelengths more efficiently than visual range wavelengths, and is in a container which has provision for allowing electromagnetic radiation to enter and be reflected back out thereof by said back-reflector, and provision for flowing gas into and out thereof, the purpose of said gas flow being to prevent deposition of contaminants onto said at least one back-reflector reflective surface.

4. A method of characterizing a sample comprising the steps of:
   a) providing an ellipsometer system comprising a source of electromagnetic radiation, a polarizer, a stage for supporting a sample, an analyzer and a detector, there optionally being at least one compensator present between said polarizer and stage and/or between said stage and analyzer;
   such than in use a beam of electromagnetism is caused to be directed by said source thereof toward a sample placed on said stage, interact with said sample, pass through said analyzer and enter said detector, said beam also passing through any present compensator,
   said source of electromagnetic radiation comprising at least one back-reflector having a reflective surface, said at least one back-reflector having a reflective surface which reflects UV wavelengths more efficiently than visual range wavelengths, and is situated in said source of electromagnetic radiation such that at least some electromagnetic radiation emitted in a direction other than that of the beam of electromagnetic radiation, is redirected into the direction of said beam of electromagnetic radiation thereby;
   said system being further characterized in that said at least one back-reflector is in a container which has provision for allowing electromagnetic radiation to enter and be reflected back out thereof by said back-reflector, and provision for flowing gas into and out thereof, the purpose of said gas flow being to prevent deposition of contaminants onto said back-reflector reflective surface;
   b) placing a sample onto said stage;
   c) simultaneously causing:
      said source of electromagnetic radiation to provide a beam of electromagnetic radiation and direct it to pass through said polarizer, interact with said sample and enter said detector, and through any compensator present;
      causing gas to flow into and out of said container;
   d) causing said detector to provide output signals which can be analyzed to characterize said sample.

5. A system for improving characteristics of a spectroscopic beam of electromagnetic radiation directed in a "forward" direction from a source of electromagnetic radiation comprising:
  an off-axis parabolic mirror; and
  a flat reflecting means;
at least one thereof having a reflective surface which reflects UV wavelengths more efficiently than visual range wavelengths;
said off-axis parabolic mirror being positioned to receive electromagnetic radiation from said source, and being positioned substantially in a "backward" projection direction 180 degrees rotated from said "forward" direction, and said flat reflecting means being positioned to receive electromagnetic radiation which reflects from said off-axis parabolic mirror and via reflection direct it directly back to said off-axis parabolic mirror, which off-axis parabolic mirror then directs it back through said source of electromagnetic radiation and along said "forward" direction;
the effect being increased intensity in said "forward" directed beam.

6. A system as in claim 5 in which said flat reflecting means uniformly reflects all wavelengths.

7. A system as in claim 5 in which said flat reflecting means reflects different wavelengths with different efficiencies.

8. A system as in claim 5 in which at least one of said flat reflecting means and said off-axis parabolic mirror reflects both IR and UV wavelengths more efficiently than visual range wavelengths.

9. A system as in claim 8 in which at least one of: said off-axis parabolic mirror and flat reflecting means comprises semiconductor.

10. A system as in claim 9 in which at least one of said off-axis parabolic mirror and flat reflecting means comprises silicon.

11. A system as in claim 10 in which said flat reflecting means comprises silicon with a thin film of other material on its reflective surface.

12. A system as in claim 11 in which said thin film of other material on said reflective surface is SiO2.

13. A system as in claim 5 which further comprises provision for flowing gas over at least one of said off-axis parabolic mirror and flat reflecting means to prevent deposition of contaminants onto said back-reflector reflective surface.

14. A system for improving characteristics of a spectroscopic beam of electromagnetic radiation directed in a "forward" direction from a source of electromagnetic radiation comprising:
  a concave mirror;
said concave mirror being positioned to receive electromagnetic radiation from said source, and being positioned substantially in a "backward" projection direction 180 degrees rotated from said "forward" direction and having a reflective surface which reflects UV wavelengths more efficiently than visual range wavelengths;
such that electromagnetic radiation from said source thereof which is directed in the "backward" direction is reflected from said concave mirror in a "forward" direction;
the effect being increased intensity in said "forward" directed beam.

15. A system as in claim 14 in which said concave mirror comprises of semiconductor.

16. A system as in claim 15 in which said concave mirror comprises silicon.

17. A system as in claim 16 in which said concave mirror comprises silicon with a thin film of other material on its reflective surface.

18. A system as in claim 17 in which said thin film of other material on said reflective surface is SiO2.

19. A system as in claim 14 which further comprises provision for flowing gas over said concave mirror surface to prevent deposition of contaminants onto said back-reflector reflective surface.

20. A system for improving characteristics of a spectroscopic beam of electromagnetic radiation directed in a "forward" direction from a source of electromagnetic radiation comprising:
  a flat reflecting means; and
  a spherical mirror;
at least one thereof having a reflective surface which reflects UV wavelengths more efficiently than visual range wavelengths;
said flat reflecting means being positioned to receive electromagnetic radiation from said source, and being positioned substantially in a "backward" projection direction 180 degrees rotated from said "forward" direction, and said spherical mirror being positioned to receive electromagnetic radiation which reflects from said flat reflecting means and via reflection direct it directly back to said flat reflecting means, which flat reflecting means then directs it back through said source of electromagnetic radiation and along said "forward" direction;
the effect being increased intensity in said "forward" directed beam.

21. A system as in claim 20 in which said flat reflecting means substantially uniformly reflects all wavelengths.

22. A system as in claim 20 in which said flat reflecting means reflects different wavelengths with different efficiencies.

23. A system as in claim 22 in which said flat reflecting means reflects IR and UV wavelengths more efficiently than visual range wavelengths.

24. A system as in claim 20 in which at least one of said flat reflecting means and spherical mirror comprises semiconductor.

25. A system as in claim 24 in which at least one of said flat reflecting means and spherical mirror comprises silicon.

26. A system as in claim 20 in which at least one of said flat reflecting means and spherical mirror comprises silicon with a thin film of other material on its reflective surface.

27. A system as in claim 26 in which said thin film of other material on said reflective surface is SiO2.

28. A system as in claim 20 which further comprises provision for flowing gas over at least one of said flat reflecting means and spherical mirror to prevent deposition of contaminants onto said back-reflector reflective surface.

* * * * *